(12) United States Patent
Osetinsky

(10) Patent No.: US 10,614,912 B2
(45) Date of Patent: Apr. 7, 2020

(54) SYSTEMS AND METHODS FOR COMPARING NETWORKS, DETERMINING UNDERLYING FORCES BETWEEN THE NETWORKS, AND FORMING NEW METACLUSTERS WHEN SATURATION IS MET

(71) Applicant: Bridget Osetinsky, New York, NY (US)

(72) Inventor: Bridget Osetinsky, New York, NY (US)

(73) Assignee: Hyperfine, LLC, New York, NY (US)

( * ) Notice: Subject to any disclaimer, the term of this patent is extended or adjusted under 35 U.S.C. 154(b) by 0 days.

(21) Appl. No.: 14/828,189

(22) Filed: Aug. 17, 2015

(65) Prior Publication Data
US 2018/0046762 A1    Feb. 15, 2018

Related U.S. Application Data

(60) Provisional application No. 62/038,352, filed on Aug. 17, 2014.

(51) Int. Cl.
*G06F 16/00* (2019.01)
*G16H 10/60* (2018.01)
*G06F 16/28* (2019.01)
*G16B 5/00* (2019.01)
*G16B 40/00* (2019.01)

(52) U.S. Cl.
CPC ........... *G16H 10/60* (2018.01); *G06F 16/285* (2019.01); *G16B 5/00* (2019.02); *G16B 40/00* (2019.02)

(58) Field of Classification Search
CPC combination set(s) only.
See application file for complete search history.

(56) References Cited

U.S. PATENT DOCUMENTS

| | | | |
|---|---|---|---|
| 6,460,036 B1 * | 10/2002 | Herz | G06Q 30/02 707/748 |
| 7,493,252 B1 | 2/2009 | Nagano et al. | |
| 8,171,032 B2 * | 5/2012 | Herz | G06Q 30/02 707/748 |

(Continued)

FOREIGN PATENT DOCUMENTS

| | | |
|---|---|---|
| EP | 2755171 A1 | 7/2014 |
| WO | 2011153171 A3 | 12/2011 |

OTHER PUBLICATIONS

Bickel, Steffan et al., "Multi-View Clustering," Proceedings of the IEEE International Conference on Data Mining, 2004 (8 pages).

(Continued)

*Primary Examiner* — Farhan M Syed
(74) *Attorney, Agent, or Firm* — Patent Capital Group

(57) ABSTRACT

The Comprehension Normalization Method for Networks, compares edge construction to edge construction between networks looking for underlying rules/forces in common between two edge constructions. It begins with the clusters from two or more networks as the two or more sides of the comparison and it uses the membership of nodes united by the cluster as proxies for the qualities of the underlying forces. If there are underlying forces in common between the networks, the method will group the original clusters into larger metaclusters of the rules in common.

20 Claims, 44 Drawing Sheets

Same Or Similar Nodes, Different Edges

Network 1

N 1-5

Connected by Edge Construction X

Network 2

N 1-5

Connected by Edge Construction Y

(56) References Cited

U.S. PATENT DOCUMENTS

| | | | |
|---|---|---|---|
| 8,826,438 B2* | 9/2014 | Perdisci | G06F 21/56 |
| | | | 726/24 |
| 9,037,589 B2* | 5/2015 | Anderson | G06F 16/3338 |
| | | | 707/737 |
| 9,230,280 B1* | 1/2016 | Maag | G06Q 40/00 |
| 9,361,806 B2 | 6/2016 | Osetinsky | |
| 2003/0037041 A1* | 2/2003 | Hertz | G06Q 30/02 |
| 2004/0161150 A1 | 8/2004 | Cukierman et al. | |
| 2006/0230109 A1 | 10/2006 | Lee et al. | |
| 2007/0038620 A1* | 2/2007 | Ka | G06F 16/951 |
| 2007/0266015 A1* | 11/2007 | Shakib | G06F 16/338 |
| 2008/0016046 A1* | 1/2008 | Guha | G06F 16/954 |
| 2010/0076979 A1* | 3/2010 | Wang | G06F 16/951 |
| | | | 707/740 |
| 2011/0276607 A1 | 11/2011 | Suma et al. | |
| 2011/0283361 A1* | 11/2011 | Perdisci | G06F 21/56 |
| | | | 726/24 |
| 2012/0072859 A1 | 3/2012 | Wang et al. | |
| 2012/0284199 A1 | 11/2012 | Lundberg | |
| 2013/0124474 A1* | 5/2013 | Anderson | G06F 16/24534 |
| | | | 707/634 |
| 2013/0124524 A1* | 5/2013 | Anderson | G06F 16/20 |
| | | | 707/737 |
| 2013/0232263 A1* | 9/2013 | Kelly | H04L 43/10 |
| | | | 709/224 |
| 2013/0254238 A1 | 9/2013 | Yon et al. | |
| 2014/0199666 A1 | 7/2014 | Osetinsky | |
| 2014/0200989 A1 | 7/2014 | Kassko et al. | |
| 2016/0048556 A1* | 2/2016 | Kelly | G06F 16/9535 |
| | | | 707/767 |

OTHER PUBLICATIONS

Chaudhuri, Kamalika, "Multi-View Clustering via Canonical Correlation Analysis," Proceedings of the 26th International Conference on Machine Learning, Montreal, Canada, 2009 (8 pages).

European Patent Office Extended Search Report and Written Opinion in EP Application Serial No. 14151168.3 dated May 22, 2014.

Hongzhe Liu et al., "A Novel Vector Space Model for Tree Based Concept Similarity Measurement," Information Management and Engineering (ICIME) 2010, The 2nd IEEE International Conference on, IEEE, Piscataway, NJ, USA, Apr. 16, 2010 (pp. 144-148). XP031684553, ISBN: 978-1-4244-5263-7.

Iosif et al., "Unsupervised Semantic Similarity Computation between Terms Using Web Documents", IEEE Transactions on Knowledge and Data Engineering, IEEE Service Center, Los Alamitos, CA, US, vol. 22, No. 11, Nov. 1, 2010 (pp. 1637-1647), XP011296670, ISSN: 1041-4347.

Jennifer S. Trueblood et al., "A Quantum Probability Account of Order Effects in Inference," Cognitive Science, vol. 35, No. 8, Sep. 26, 2011 (pp. 1518-1552), XP055114980, ISSN: 0364-0213, DOI: 10.1111/1.1551-6709.2011.01197.x.

Jiao et al., "An agent-based framework for collaborative negotiation in the global manufacturing supply chain network", Robotics and Computer-Integrated Manufacturing 22 (2006) 239-255.

Ladau et al., "Incremental String Comparison", SIAM, 1998, pp. 29.

Lawrie, Dawn et al., "Expanding Identifiers to Normalize Source Code Vocabulary," Loyola University Maryland, 2011 27th IEEE International Conference on Software Maintenance (ISCM), (10 pages).

Maderia, Sara C. et al., "Biclustering Algorithms for Biological Data Analysis: A Survey," IEEE Transactions on Computational Biology and Bioinformatics, vol. 1, No. 1, Jan.-Mar. 2004 (22 pages).

Monti, Stefano, "Consensus Clustering, A resampling-based method for class discovery and visualization of gene expression microarray data," Broad Institute/MIT Center for Genome Research, Kluwer Academics Publishers, 2003 (34 pages).

Non Final Office Action in U.S. Appl. No. 14/154,151 dated Nov. 3, 2015, 10 pages.

Notice of Allowance in U.S. Appl. No. 14/154,151 dated Feb. 12, 2016, 22 pages.

PCT International Preliminary Report on Patentability in PCT International Application Serial No. PCT/US2011/038637 dated Dec. 4, 2012.

PCT International Search Report and Written Opinion in PCT International Application Serial No. PCT/US2011/038637 dated Feb. 17, 2012.

Peng et al, "CACS: A Novel Classification Algorithm Based on Concept Similarity", Radio Frequency Identification [Lecture Notes in Computer Science], Springer Berlin, Heidelberg, Aug. 6, 2007, (pp. 500-507), XP047179926, ISSN: 0302-9743, ISBN: 978-3-642-45283-3.

Sorg et al., "Cross-lingual Information Retrieval with Explicit Semantic Analysis", CLEF, 2008, pp. 13.

Sorrentino et al. "Schema Normalization for Improving Schema Matching," Conceptual Modeling, ER 2009, Springer Berlin, Heidelberg, Nov. 9, 2009, (pp. 280-293), XP019132461, ISBN: 978-3-642-04839-5.

Xiquan et al., "A Concept Similarity Computation Based on Multi-Property Ontology," Software Engineering and Data Mining (SEDM), 2010 2nd International Conference on, IEEE, Piscataway, NJ, USA, Jun. 23, 2010 (pp. 538-543), KP031728065, ISBN: 978-1-4244-7324-3.

Xu, Chang et al., "A Survey on Multi-View Learning," arxiv:1304.5634v1; cs.lg, Apr. 20, 2013 (59 pages).

\* cited by examiner

Fig. 2
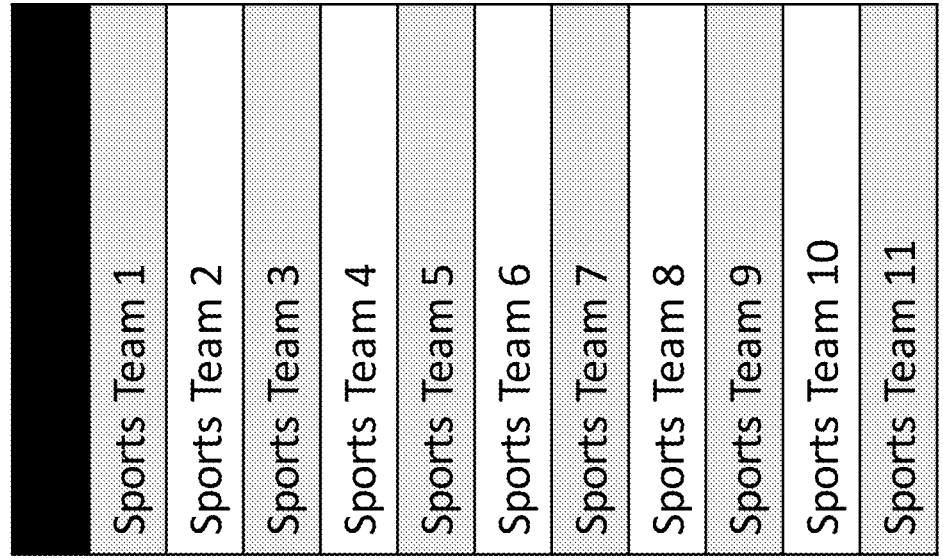
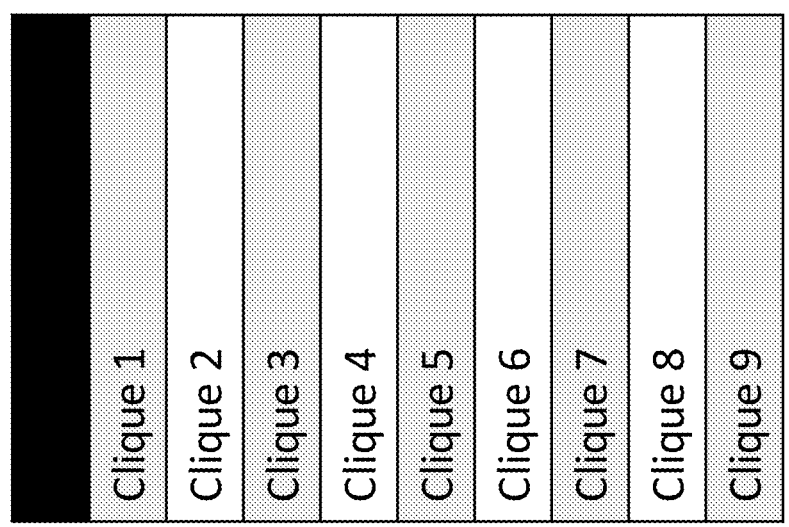

Fig. 3

Students in X school District

| School A |
|---|
| Sports Team 1 |
| Sports Team 9 |
| Sports Team 10 |

| School B |
|---|
| Sports Team 3 |
| Sports Team 4 |
| Sports Team 6 |
| Sports Team 7 |
| Sports Team 8 |
| Sports Team 11 |

| School C |
|---|
| Sports Team 2 |
| Sports Team 5 |

Students in X school District

| School A |
|---|
| Clique 4 |
| Clique 6 |

| School B |
|---|
| Clique 2 |
| Clique 5 |
| Clique 7 |
| Clique 9 |

| School C |
|---|
| Clique 1 |
| Clique 3 |
| Clique 8 |

Fig. 4A
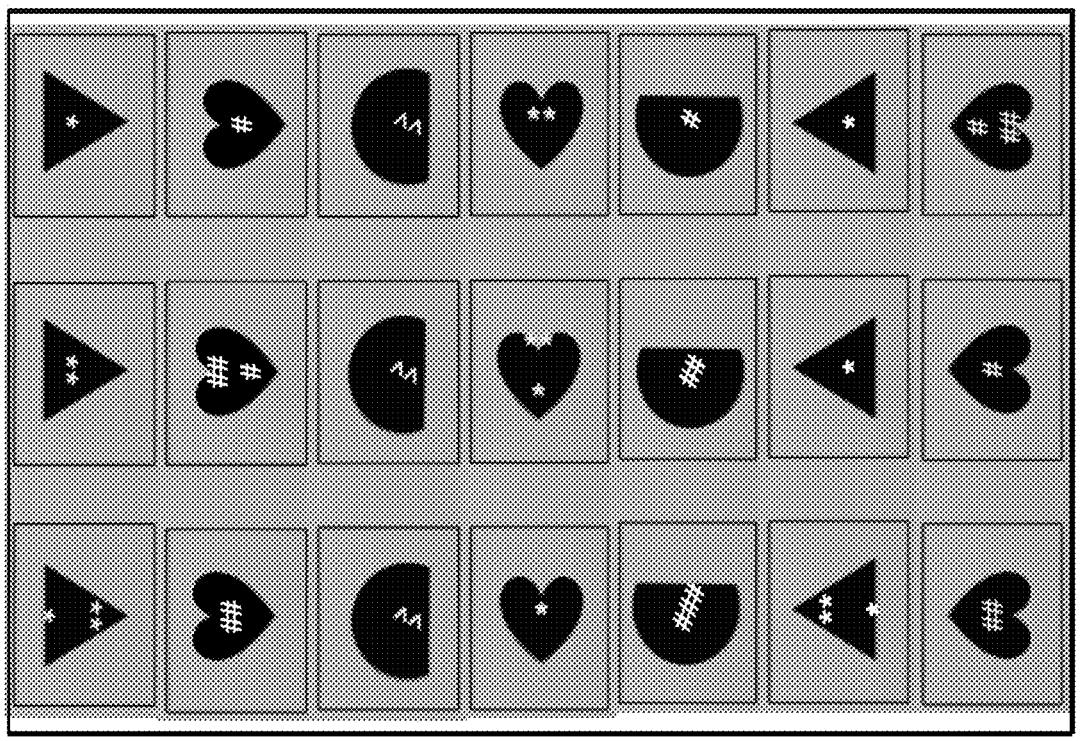
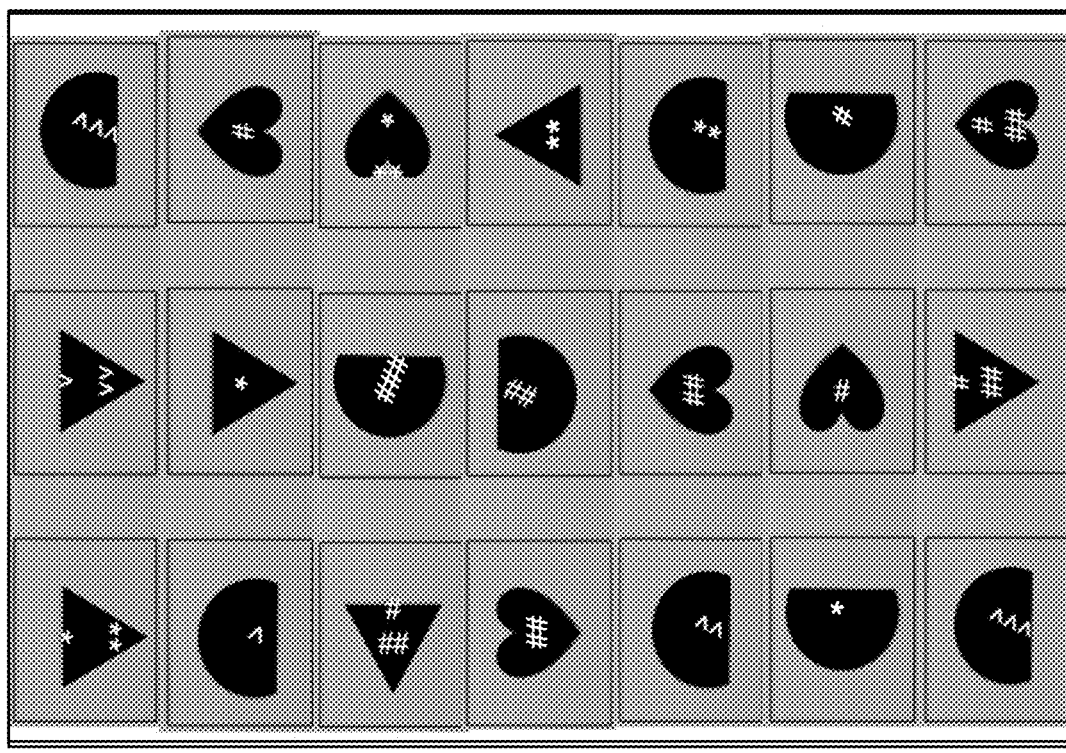

Fig. 4B

Disease Key

A. Coats Disease
B. Norrie Disease
C. Exudative Vitreoretinopathy
D. Osteopetrosis
E. Hyperostosis
F. Endosteal
G. Van Buchem Disease
H. Bone Mineral Density Variability
I. Osteoporosis Pseudoglioma Syndrom
J. Urolithiasise
K. Caffey Disease
L. Dissection of Cervical Arteries
M. Ehlers Danlos Syndrome
N. Osteogenesis Imperfecta
O. Marfan Syndrome
P. Nevo Syndrome
Q. Aneurysm
R. Familial Arterial
S. Aortic Aneurysm
T. Shprintzen Goldberg Syndrome
U. MASS Syndrome
V. Weill Marchesani Syndrome
W. Ectopia
X. Andiridia Type II
Y. Foveal hypoplasia
Z. Cataract
1. Morning Glory Disc Anomaly
2. Optic Nerve
3. Hypoplasia/Aplasia
4. Colobooma Ocular
5. Peters anomaly
6. Keratitis
7. Eye anomalies
8. Glaucoma
9. Optic Atrophy
10. 3 Methylglutaconicaciduria
11. Emphysema

Gene Disease Network (3 Unknown underlying Categorization forces: Rotation, Shape, and Symbol)

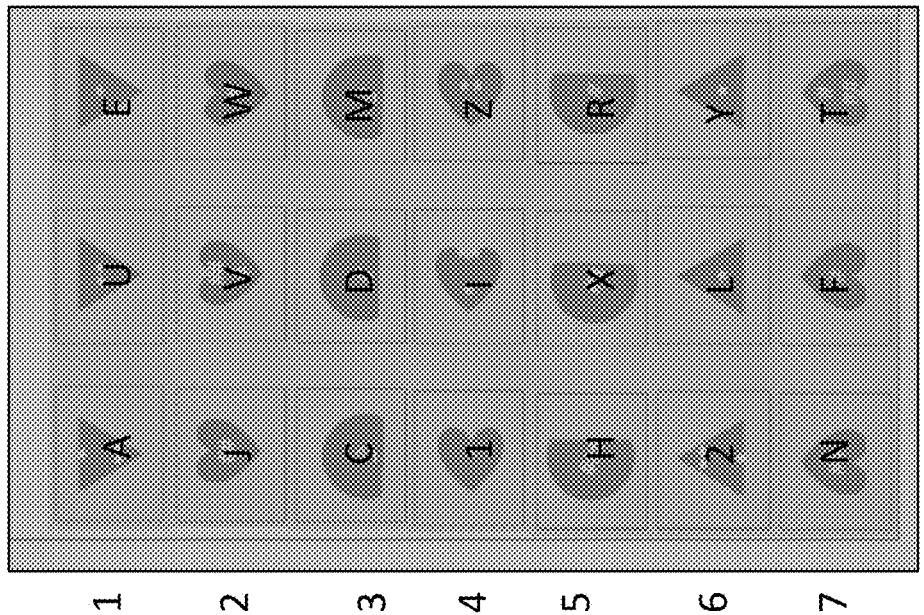

Metabolic Disease Network (2 Unknown underlying categorization forces: Rotation, and Number)

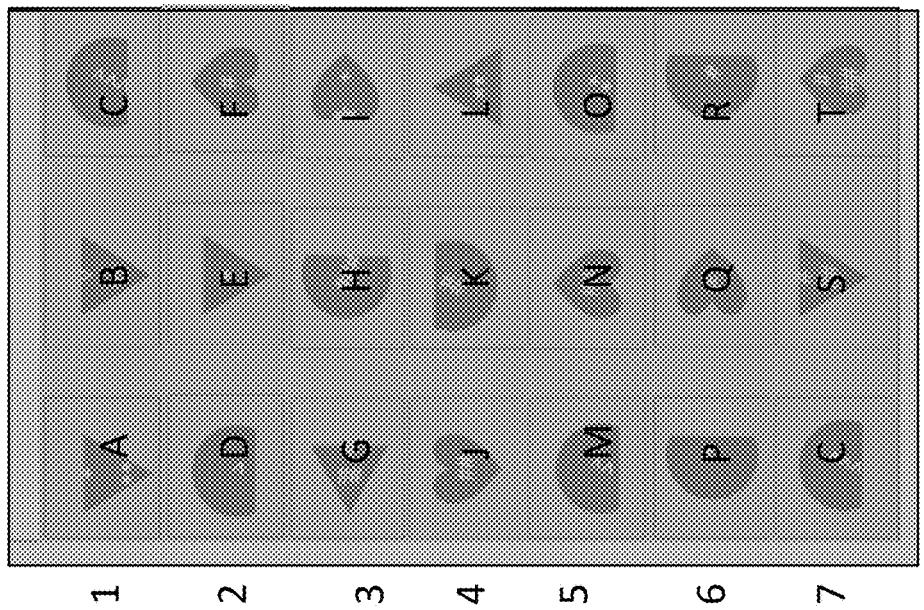

Metabolic Disease Network (2 Unknown underlying categorization forces: Rotation, and Number)

|   | A | B | C |
|---|---|---|---|
| 1 | A | B | C |
| 2 | D | E | F |
| 3 | G | H | I |
| 4 | J | K | L |
| 5 | M | N | O |
| 6 | P | Q | R |
| 7 | C | S | T |

Gene Disease Network    Fig. 4C (3 Unknown underlying categorization forces: Rotation, Shape, and Symbol)

|   | A | U | E | 1 |
|---|---|---|---|---|
| 2 | J | V | W |   |
| 3 | C | D | M |   |
| 4 | 1 | I | Z |   |
| 5 | H | X | R |   |
| 6 | 2 | L | Y |   |
| 7 | N | F | T |   |

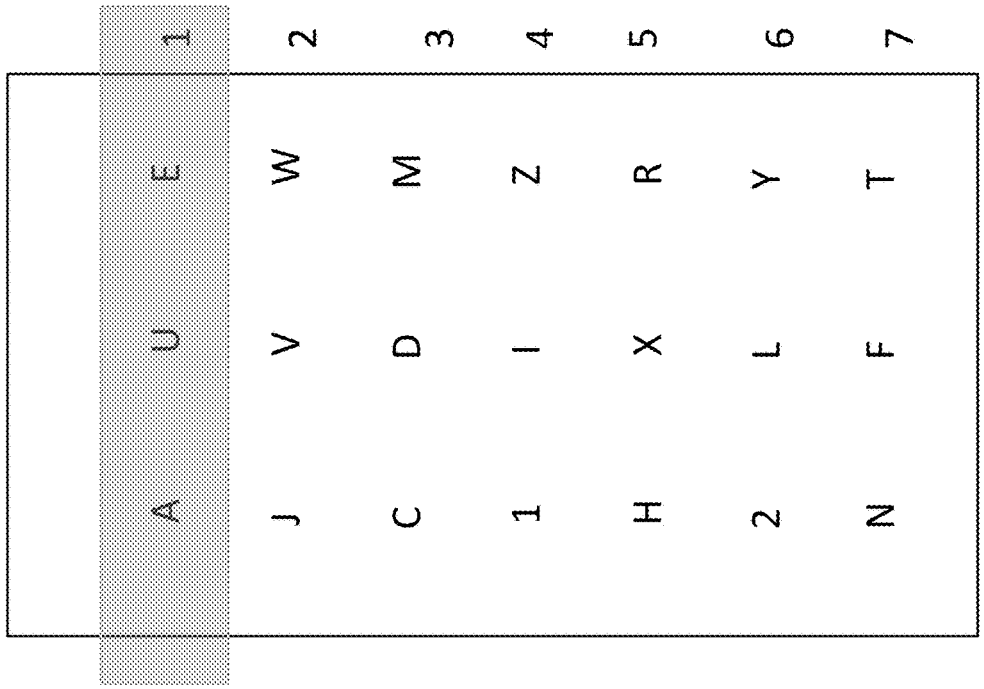
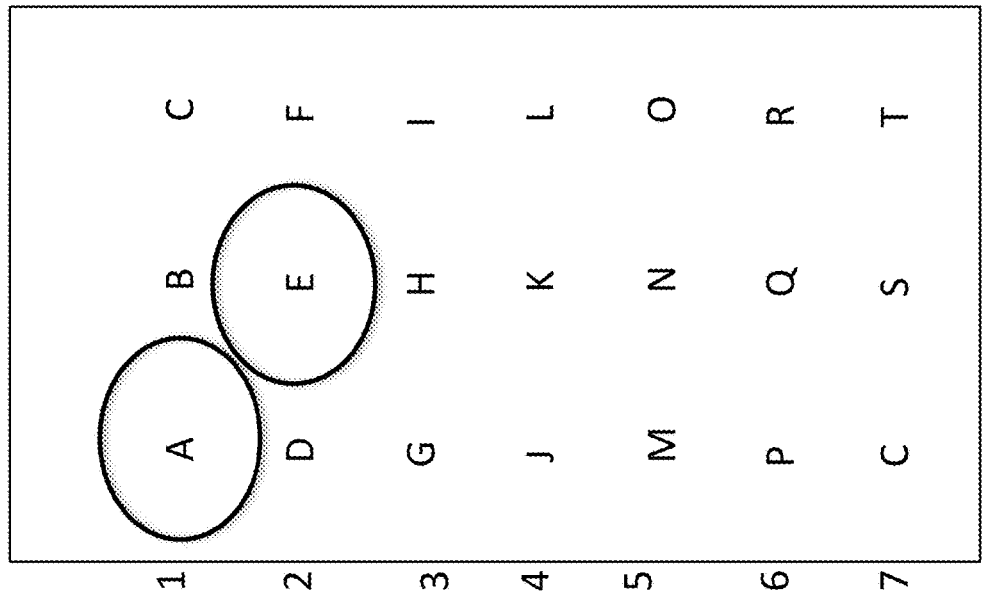

Fig. 4E

Metabolic Disease Network
(2 Unknown underlying categorization forces: Rotation, and Number)

| 1 | A | B | C |
| 2 | D | E | F |
| 3 | G | H | I |
| 4 | J | K | L |
| 5 | M | N | O |
| 6 | P | Q | R |
| 7 | C | S | T |

Gene Disease Network
(3 Unknown underlying categorization forces: Rotation, Shape, and Symbol)

| 1 | A | U | E |
| 2 | J | V | W |
| 3 | C | D | M |
| 4 | 1 | I | Z |
| 5 | H | X | R |
| 6 | 2 | L | Y |
| 7 | N | F | T |

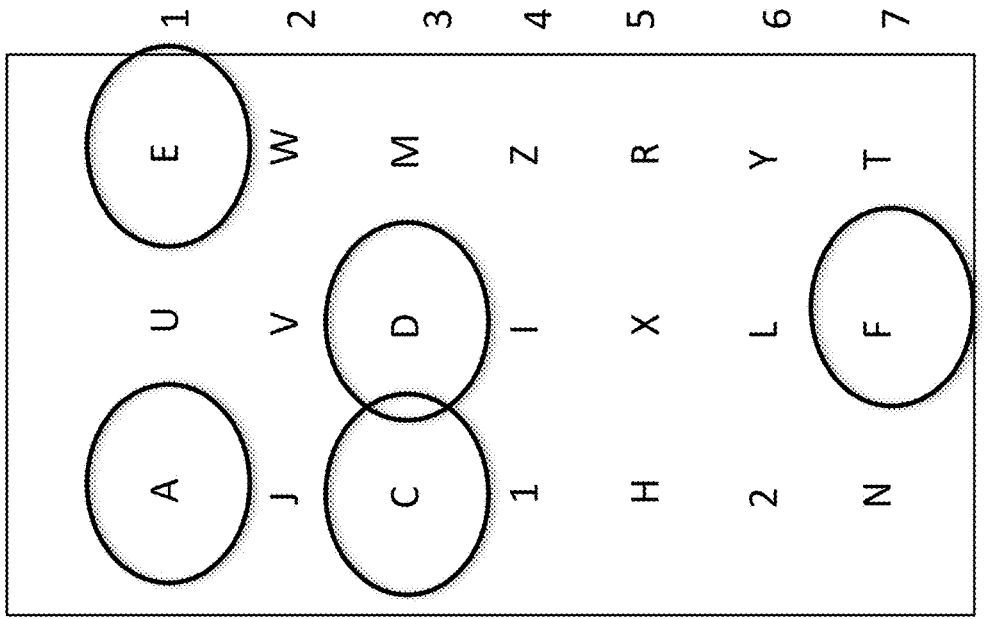
Gene Disease Network    Fig. 4F
(3 Unknown underlying categorization forces: Rotation, Shape, and Symbol)
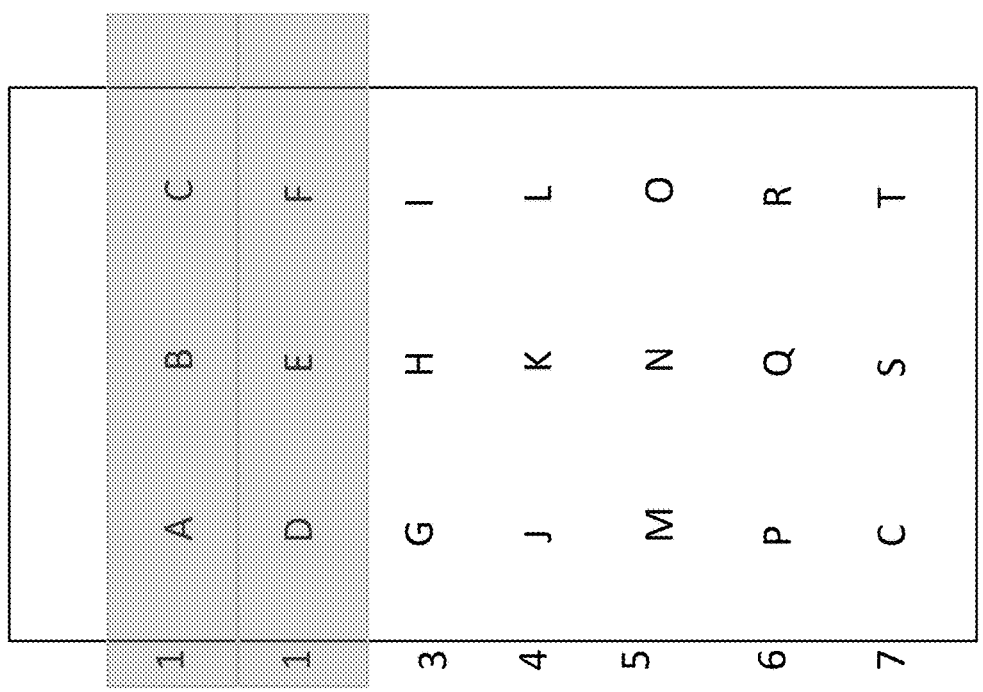
Metabolic Disease Network
(2 Unknown underlying categorization forces: Rotation, and Number)

Metabolic Disease Network (2 Unknown underlying categorization forces: Rotation, and Number)

|   | | | |
|---|---|---|---|
| 1 | A | B | C |
| 2 | D | E | F |
| 3 | G | H | I |
| 4 | J | K | L |
| 5 | M | N | O |
| 6 | P | Q | R |
| 7 | C | S | T |

Gene Disease Network        Fig. 4G (3 Unknown underlying categorization forces: Rotation, Shape, and Symbol)

|   | | | |
|---|---|---|---|
| 1 | A | U | E |
| 2 | J | V | W |
| 1 | C | D | M |
| 4 | 1 | I | Z |
| 5 | H | X | R |
| 6 | 2 | L | Y |
| 1 | N | F | T |

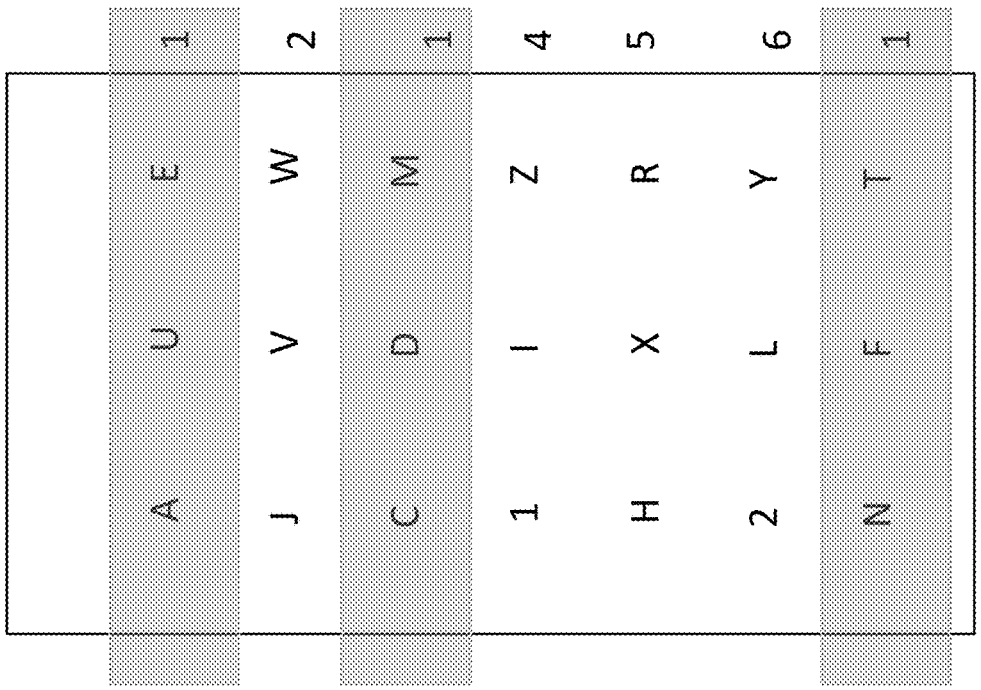
Gene Disease Network  Fig. 4H
(3 Unknown underlying categorization forces: Rotation, Shape, and Symbol)
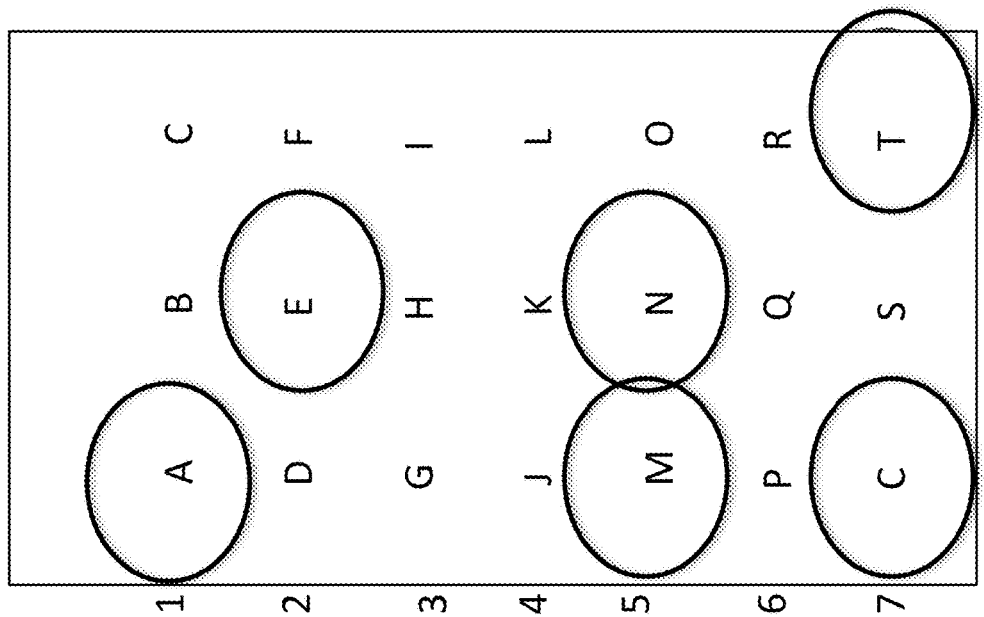
Metabolic Disease Network
(2 Unknown underlying categorization forces: Rotation, and Number)

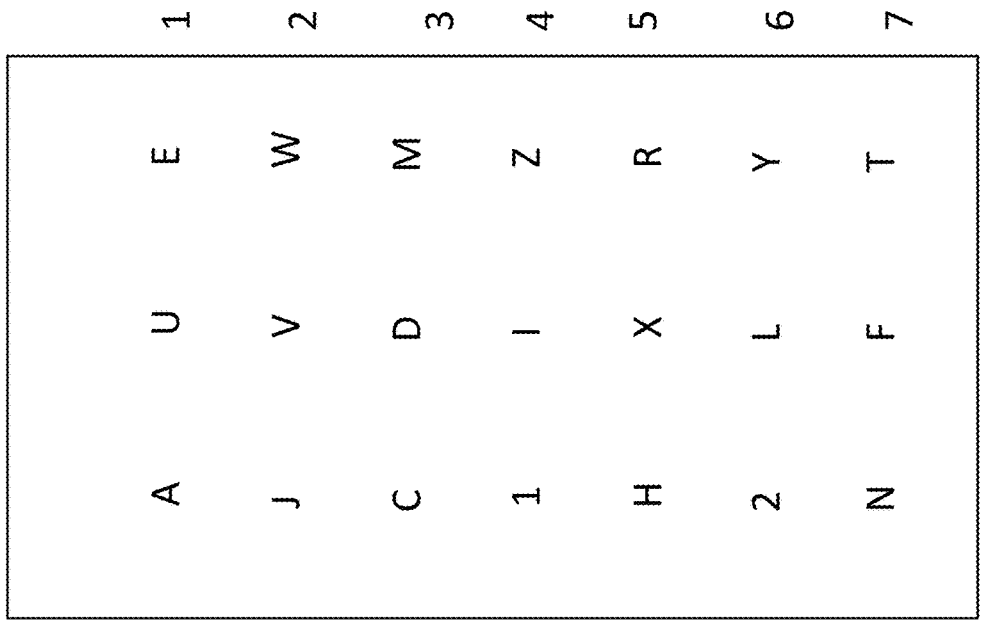
Gene Disease Network  Fig. 4I
(3 Unknown underlying categorization forces: Rotation, Shape, and Symbol)
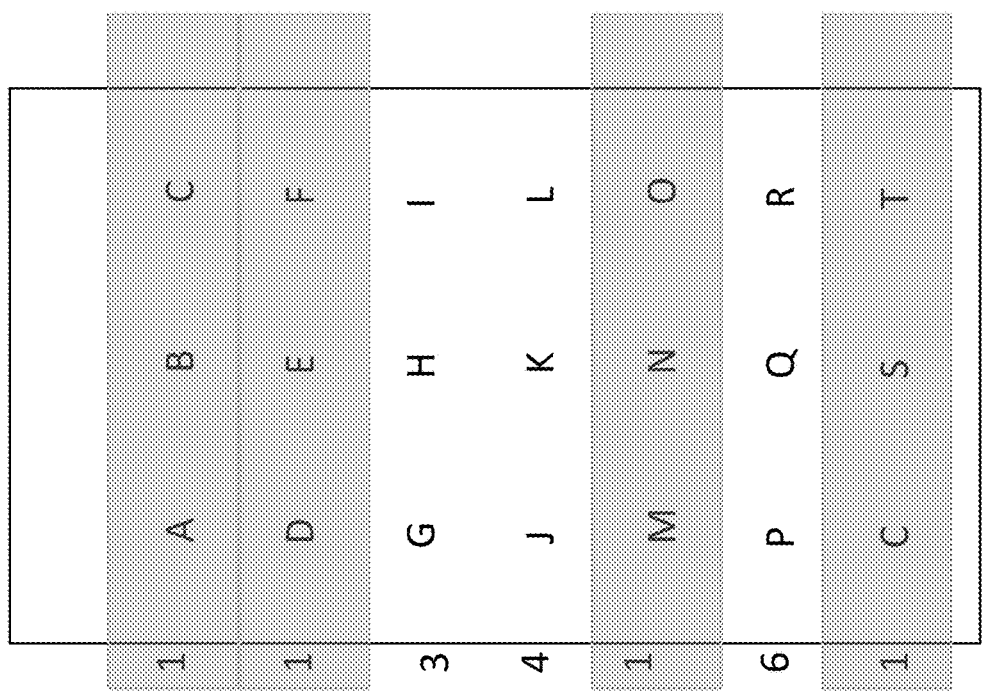
Metabolic Disease Network
(2 Unknown underlying categorization forces: Rotation, and Number)

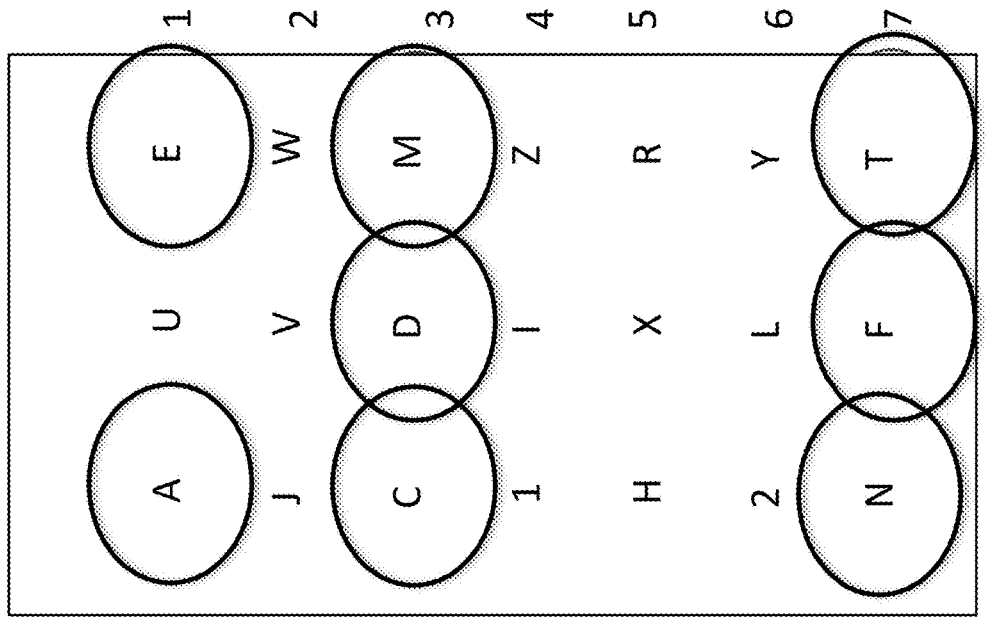
Gene Disease Network    Fig. 4J
(3 Unknown underlying categorization forces: Rotation, Shape, and Symbol)
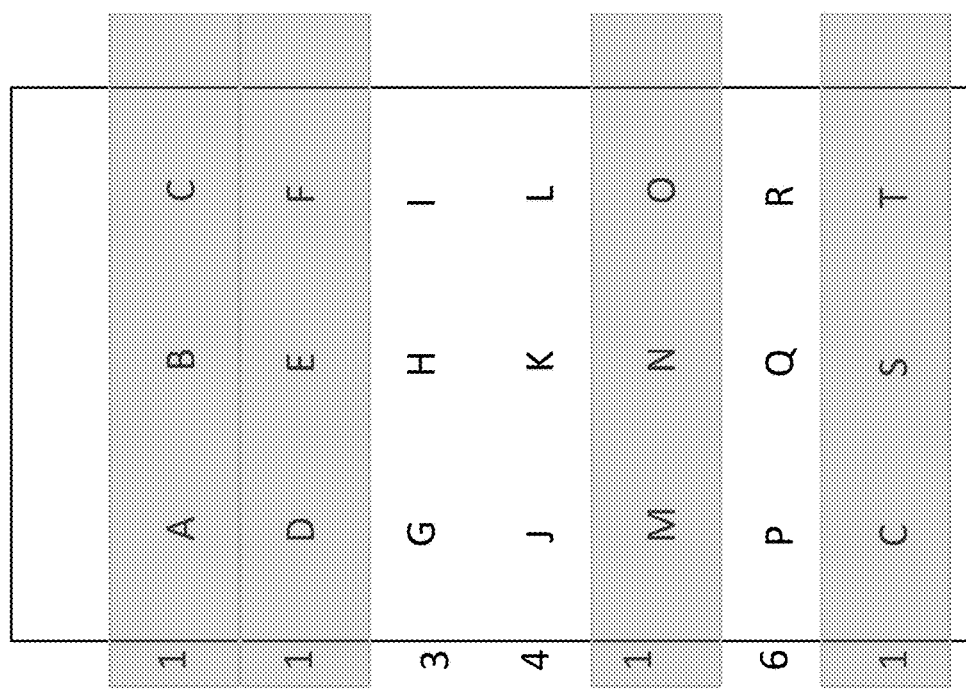
Metabolic Disease Network
(2 Unknown underlying categorization forces: Rotation, and Number)

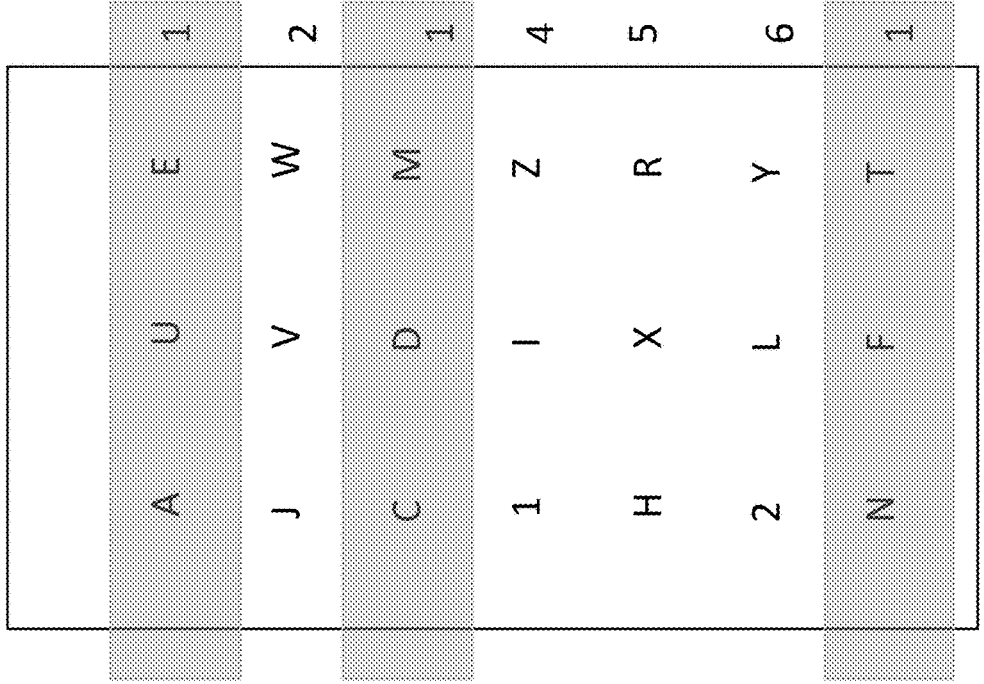
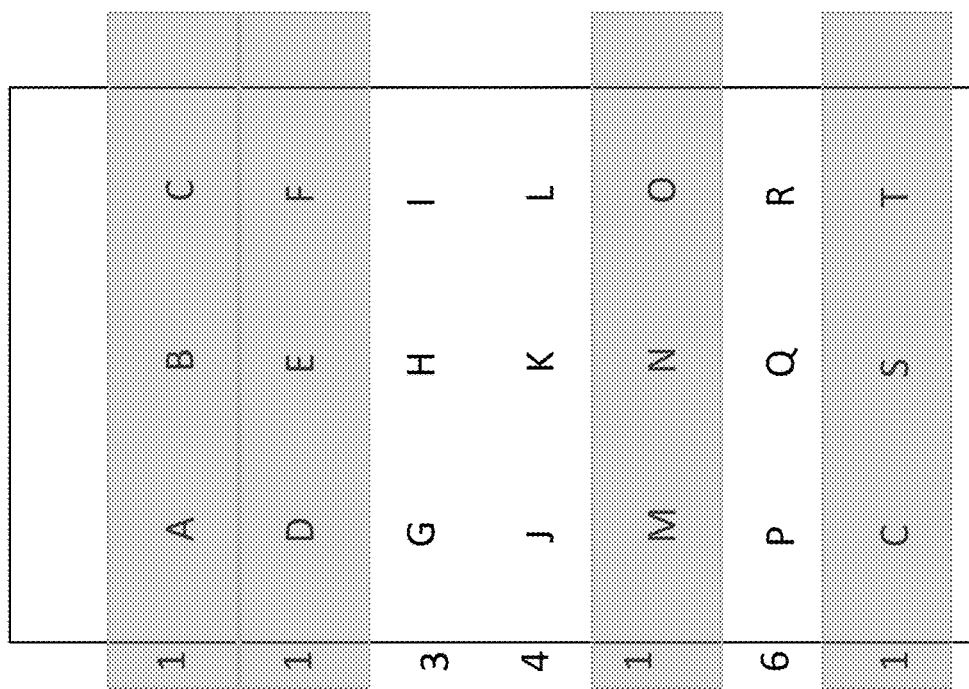
Fig. 4K

Concurrently or nonconcurrently starting with the second cluster

Fig. 4L

Metabolic Disease Network (2 Unknown underlying categorization forces: Rotation, and Number)

|   | | | |
|---|---|---|---|
| 1 | A | B | C |
| 2 | D | E | F |
| 3 | G | H | I |
| 4 | J | K | L |
| 5 | M | N | O |
| 6 | P | Q | R |
| 7 | C | S | T |

Gene Disease Network    Fig. 4M (3 Unknown underlying categorization forces: Rotation, Shape, and Symbol)

|   | A | U | E | 1 |
|---|---|---|---|---|
|   | J | V | W | 2 |
|   | C | D | M | 3 |
|   | 1 | I | Z | 4 |
|   | H | X | R | 5 |
|   | 2 | L | Y | 6 |
|   | N | F | T | 7 |

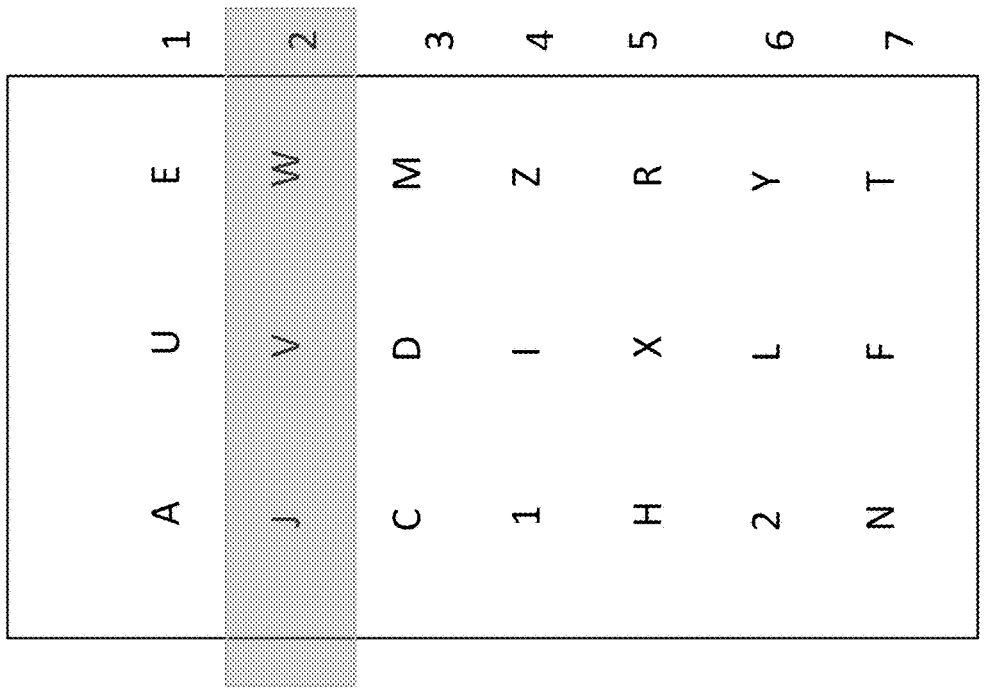
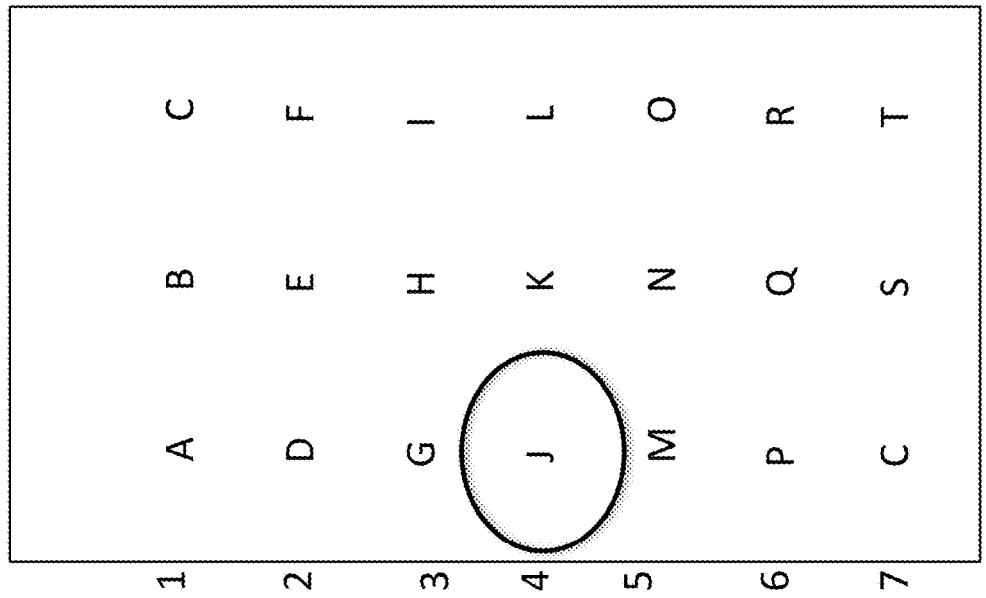

Fig. 4O

Gene Disease Network
(3 Unknown underlying categorization forces: Rotation, Shape, and Symbol)

|   |   |   |   |
|---|---|---|---|
| A | U | E | 1 |
| J | V | W | 2 |
| C | D | M | 3 |
| 1 | I | Z | 4 |
| H | X | R | 5 |
| 2 | L | Y | 6 |
| N | F | T | 7 |

Metabolic Disease Network
(2 Unknown underlying categorization forces: Rotation, and Number)

|   |   |   |   |
|---|---|---|---|
| 1 | A | B | C |
| 2 | D | E | F |
| 3 | G | H | I |
| 2a | J | K | L |
| 5 | M | N | O |
| 6 | P | Q | R |
| 7 | C | S | T |

Metabolic Disease Network

(2 Unknown underlying categorization forces: Rotation, and Number)

|   | 1 | 2 | 3 | 4 | 5 | 6 | 7 |
|---|---|---|---|---|---|---|---|
|   | A | B | C | | | | |
|   | D | E | F | | | | |
|   | G | H | I | | | | |
|   | J | K | L | | | | |
|   | M | N | O | | | | |
|   | P | Q | R | | | | |
|   | C | S | T | | | | |

Gene Disease Network     Fig. 4P (3 Unknown underlying categorization forces: Rotation, Shape, and Symbol)

|   | 1 | 2 | 3 | 4 | 5 | 6 | 7 |
|---|---|---|---|---|---|---|---|
| A | U | E | | | | | |
| J | V | W | | | | | |
| C | D | M | | | | | |
| 1 | I | Z | | | | | |
| H | X | R | | | | | |
| 2 | L | Y | | | | | |
| N | F | T | | | | | |

Fig. 4Q

Metabolic Disease Network

(2 Unknown underlying categorization forces: Rotation, and Number)

|   | | | |
|---|---|---|---|
| 1 | A | B | C |
| 2 | D | E | F |
| 3 | G | H | I |
| 4 | J | K | L |
| 5 | M | N | O |
| 6 | P | Q | R |
| 7 | C | S | T |

Gene Disease Network

(3 Unknown underlying categorization forces: Rotation, Shape, and Symbol)

|   | | | |
|---|---|---|---|
| 1 | A | U | E |
| 2 | J | V | W |
| 3 | C | D | M |
| 4 | 1 | I | Z |
| 5 | H | X | R |
| 6 | 2 | L | Y |
| 7 | N | F | T |

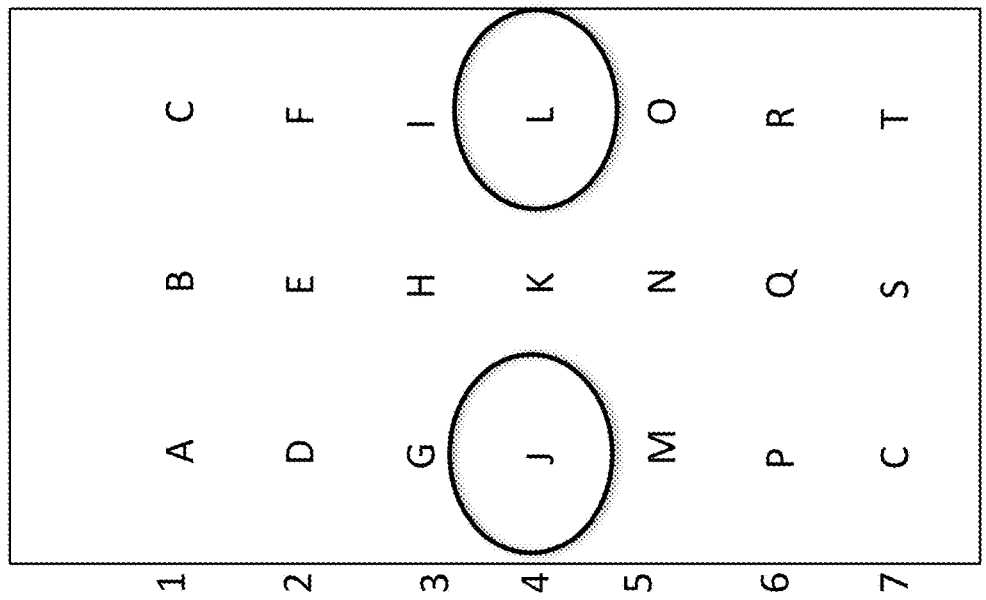

Fig. 4S

Metabolic Disease Network    SATURATION (2 Unknown underlying categorization forces: Rotation, and Number)

|   | 1 | 2 | 3 |
|---|---|---|---|
| 1 | A | B | C |
| 2 | D | E | F |
| 3 | G | H | I |
| 4 | J | K | L |
| 5 | M | N | O |
| 6 | P | Q | R |
| 7 | C | S | T |

Column 4 (K) is shaded.

Gene Disease Network

(3 Unknown underlying categorization forces: Rotation, Shape, and Symbol)

|   | 1 | 2 | 3 |
|---|---|---|---|
| 1 | A | U | E |
| 2 | J | V | W |
| 3 | C | D | M |
| 4 | 1 | I | Z |
| 5 | H | X | R |
| 6 | 2 | L | Y |
| 7 | N | F | T |

Columns 2 and 6 are shaded.

Fig. 4T

And also concurrently or nonconcurrently beginning with the third cluster

Fig. 4U

Metabolic Disease Network
(2 Unknown underlying categorization forces: Rotation, and Number)

| | | | |
|---|---|---|---|
| 1 | A | B | C |
| 2 | D | E | F |
| 3 | G | H | I |
| 4 | J | K | L |
| 5 | M | N | O |
| 6 | P | Q | R |
| 7 | C | S | T |

Gene Disease Network
(3 Unknown underlying categorization forces: Rotation, Shape, and Symbol)

| | 1 | 2 | 3 | 4 | 5 | 6 | 7 |
|---|---|---|---|---|---|---|---|
| | A | J | C | 1 | H | 2 | N |
| | U | V | D | I | X | L | F |
| | E | W | M | Z | R | Y | T |

Fig. 4V

Metabolic Disease Network
(2 Unknown underlying categorization forces: Rotation, and Number)

|   | 1 | 2 | 3 | 4 |
|---|---|---|---|---|
| 1 | A | B | C |   |
| 2 | D | E | F |   |
| 3 | G | H | I |   |
| 4 | J | K | L |   |
| 5 | M | N | O |   |
| 6 | P | Q | R |   |
| 7 | C | S | T |   |

Gene Disease Network
(3 Unknown underlying categorization forces: Rotation, Shape, and Symbol)

|   | 1 | 2 | 3 | 4 | 5 |
|---|---|---|---|---|---|
| 1 | A | U | E |   |   |
| 2 | J | V | W |   |   |
| 3 | C | D | M |   |   |
| 4 | 1 | I | Z |   |   |
| 5 | H | X | R |   |   |
| 6 | 2 | L | Y |   |   |
| 7 | N | F | T |   |   |

Gene Disease Network     Fig. 4W (3 Unknown underlying categorization forces: Rotation, Shape, and Symbol)

|   | | | |
|---|---|---|---|
| 1 | A | U | E |
| 2 | J | V | W |
| 3 | C | D | M |
| 4 | 1 | I | Z |
| 5 | H | X | R |
| 6 | 2 | L | Y |
| 7 | N | F | T |

Metabolic Disease Network (2 Unknown underlying categorization forces: Rotation, and Number)

|   | | | |
|---|---|---|---|
| 1 | A | B | C |
| 2 | D | E | F |
| 3 | G | H | I |
| 4 | J | K | L |
| 5 | M | N | O |
| 6 | P | Q | R |
| 7 | C | S | T |

Fig. 4X

Metabolic Disease Network
(2 Unknown underlying categorization forces: Rotation, and Number)

|   | 1 | 2 | 3 |
|---|---|---|---|
| 1 | A | B | C |
| 2 | D | E | F |
| 3 | G | H | I |
| 4 | J | K | L |
| 5 | M | N | O |
| 6 | P | Q | R |
| 7 | C | S | T |

Gene Disease Network
(3 Unknown underlying categorization forces: Rotation, Shape, and Symbol)

|   | 1 | 2 | 3 |
|---|---|---|---|
| 1 | A | U | E |
| 2 | J | V | W |
| 3 | C | D | M |
| 4 | 1 | I | Z |
| 5 | H | X | R |
| 6 | 2 | L | Y |
| 7 | N | F | T |

Fig. 4Y

Metabolic Disease Network
(2 Unknown underlying categorization forces: Rotation, and Number)

|   | 1 | 2 | 3 |
|---|---|---|---|
| 1 | A | B | C |
| 2 | D | E | F |
| 3 | G | H | I |
| 4 | J | K | L |
| 5 | M | N | O |
| 6 | P | Q | R |
| 7 | C | S | T |

Gene Disease Network
(3 Unknown underlying categorization forces: Rotation, Shape, and Symbol)

|   | 1 | 2 | 3 |
|---|---|---|---|
| 1 | A | U | E |
| 2 | J | V | W |
| 3 | C | D | M |
| 4 | 1 | I | Z |
| 5 | H | X | R |
| 6 | 2 | L | Y |
| 7 | N | F | T |

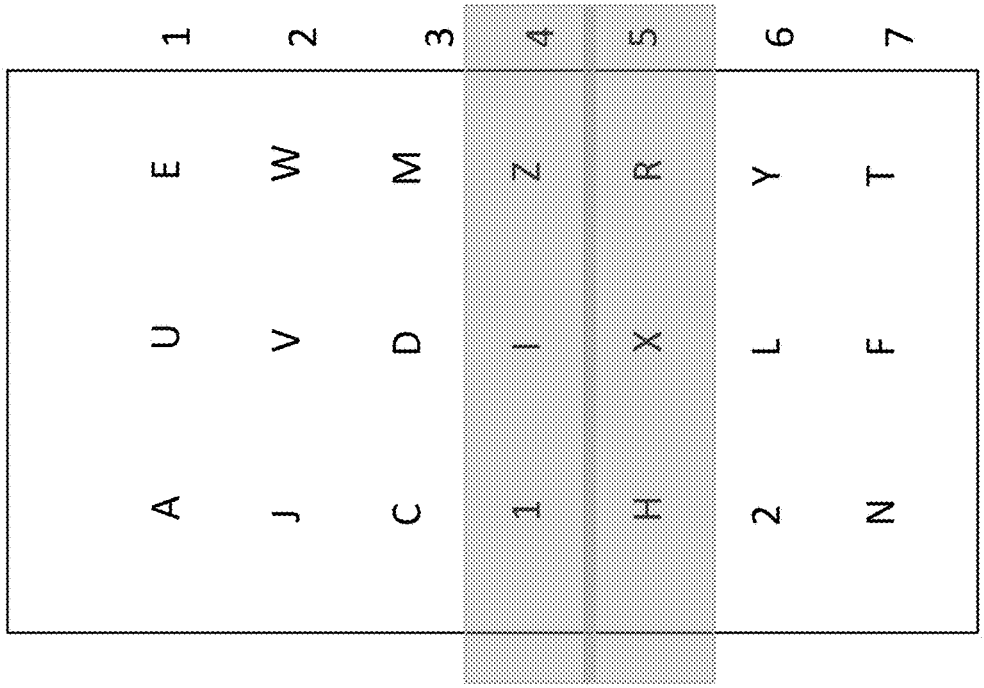
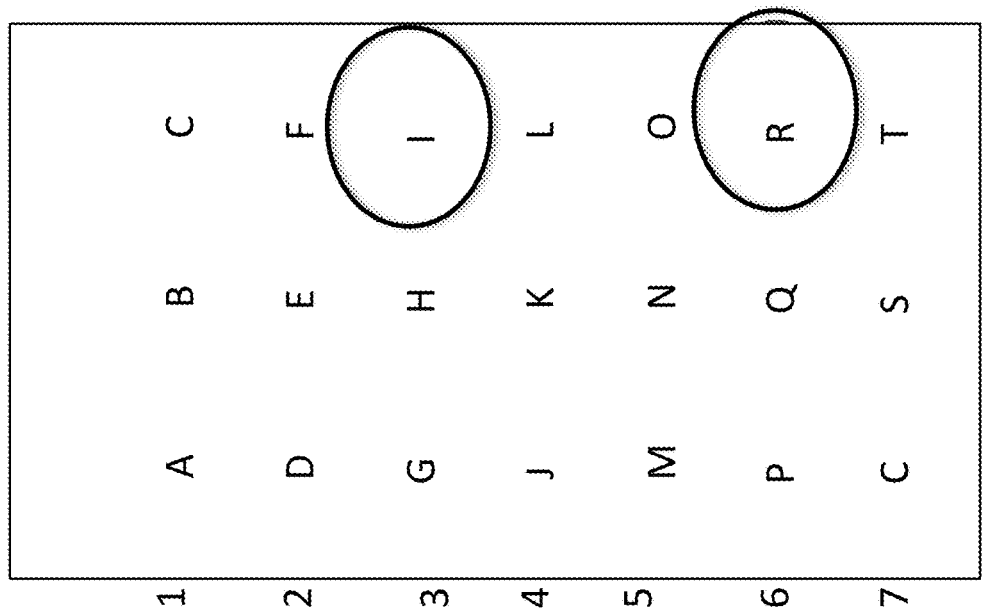
Fig. 4Z

Fig. 4AA

Metabolic Disease Network
(2 Unknown underlying categorization forces: Rotation, and Number)

| | | | |
|---|---|---|---|
| 1 | A | B | C |
| 2 | D | E | F |
| 3 | G | H | I |
| 4 | J | K | L |
| 5 | M | N | O |
| 6 | P | Q | R |
| 7 | C | S | T |

Gene Disease Network
(3 Unknown underlying categorization forces: Rotation, Shape, and Symbol)

| | | | |
|---|---|---|---|
| 1 | A | U | E |
| 2 | J | V | W |
| 3 | C | D | M |
| 4 | 1 | I | Z |
| 5 | H | X | R |
| 6 | 2 | L | Y |
| 7 | N | F | T |

Metabolic Disease Network — SATURATION

(2 Unknown underlying categorization forces: Rotation, and Number)

| | | | |
|---|---|---|---|
| 1 | A | B | C |
| 2 | D | E | F |
| 3 | G | H | I |
| 4 | J | K | L |
| 5 | M | N | O |
| 6 | P | Q | R |
| 7 | C | S | T |

Gene Disease Network     Fig. 4CC (3 Unknown underlying categorization forces: Rotation, Shape, and Symbol)

| | | | |
|---|---|---|---|
| 1 | A | U | E |
| 2 | J | V | W |
| 3 | C | D | M |
| 4 | 1 | I | Z |
| 5 | H | X | R |
| 6 | 2 | L | Y |
| 7 | N | F | T |

Fig. 4DD

When there are two data sets that share a same underlying force The Comprehension Normalization Method will group the data set by different qualities of the force in common

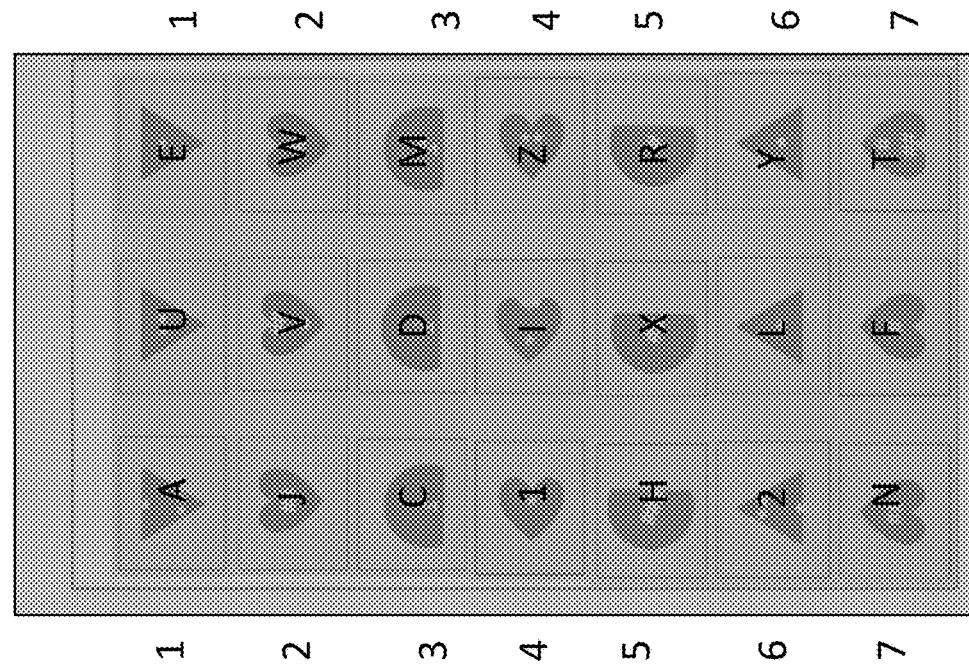
Gene Disease Network  Fig. 4EE
(3 Unknown underlying categorization forces: Rotation, Shape, and Symbol)
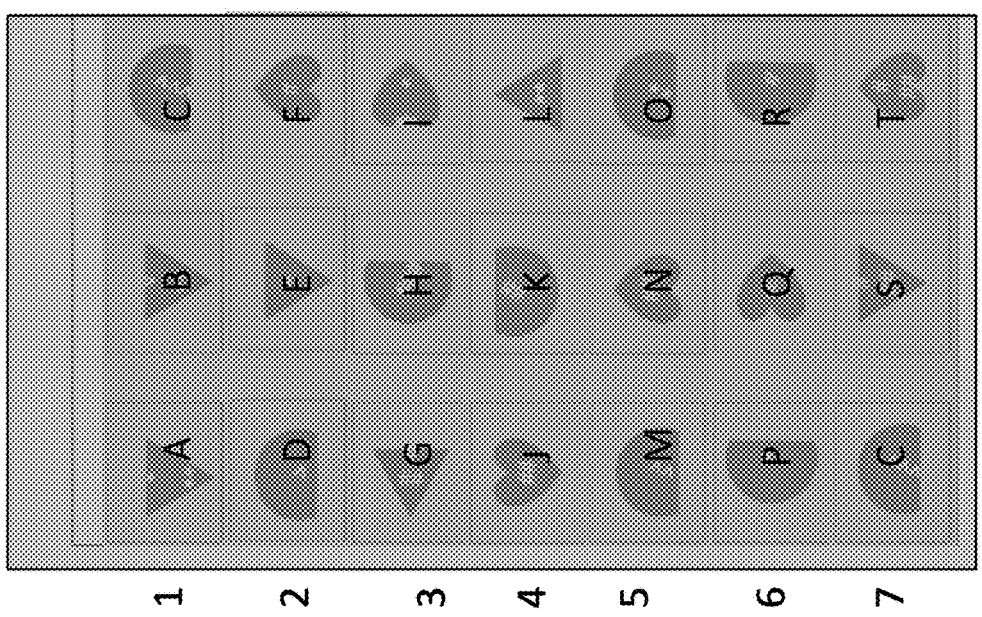
Metabolic Disease Network
(2 Unknown underlying categorization forces: Rotation, and Number)

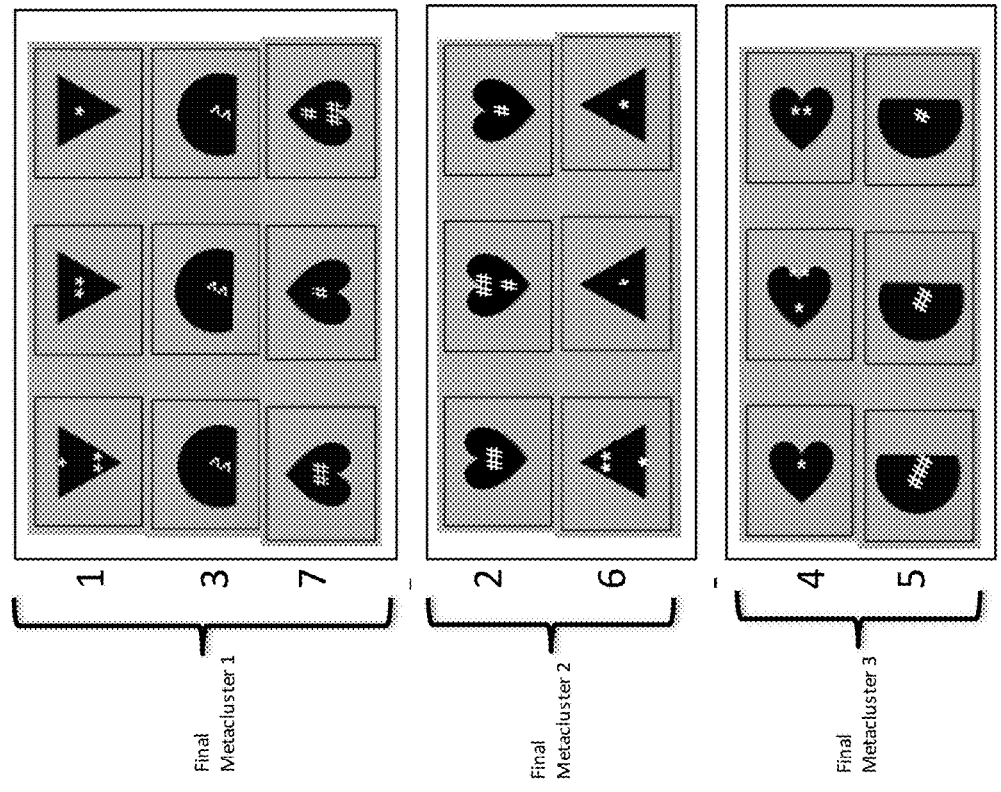
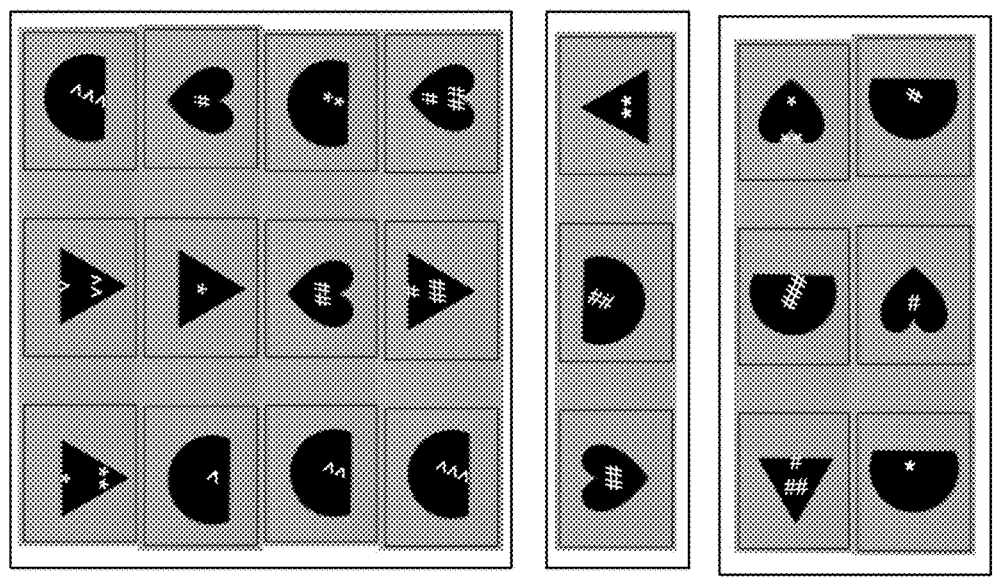
Fig. 4FF

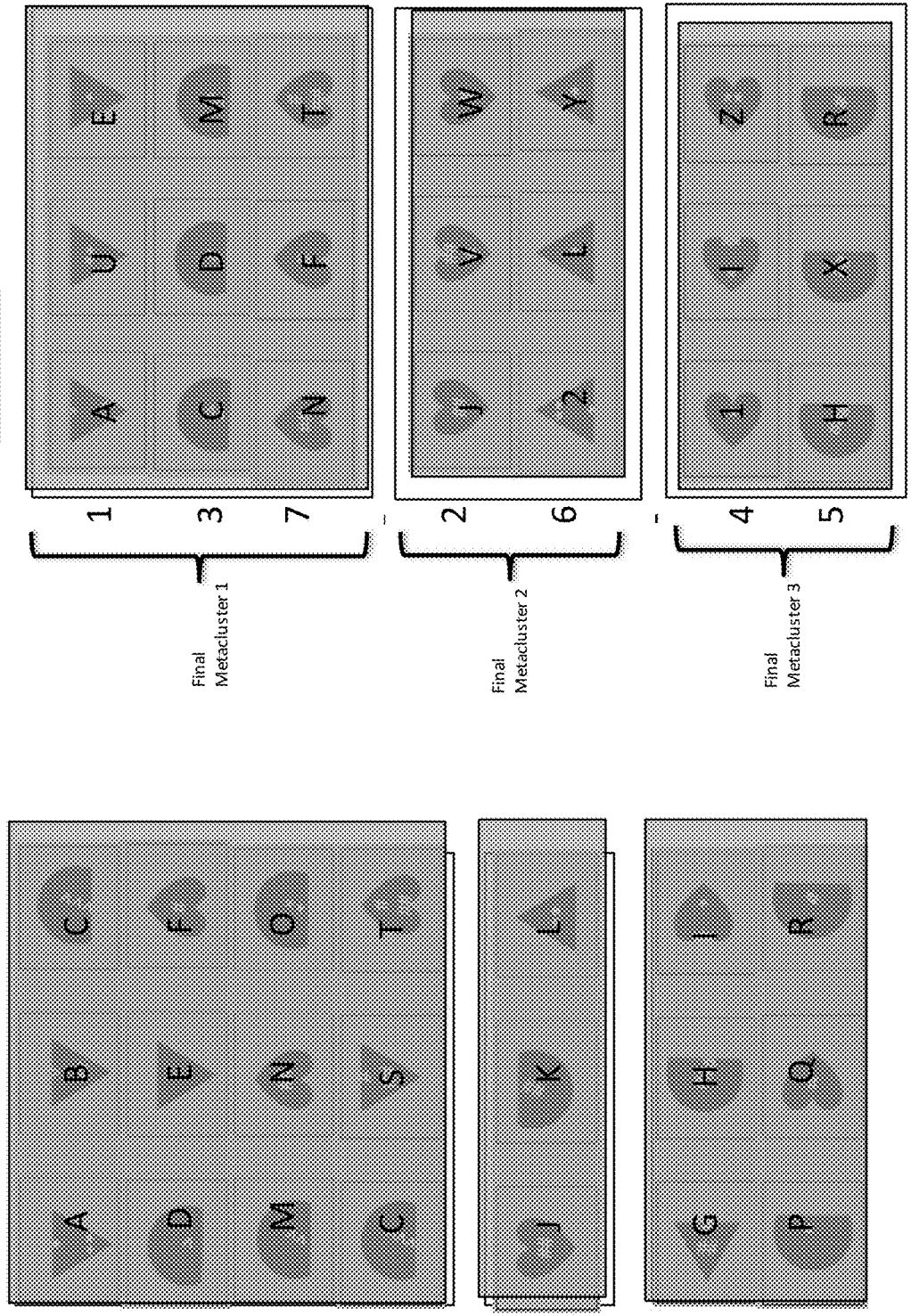

Fig. 4II

Gene Disease Network (3 Unknown underlying categorization forces: Rotation, Shape, and Symbol)

Final Metacluster 1

Final Metacluster 2

Final Metacluster 3

Instead of grouping by color it will group by shape miRNA Disease Network (2 Unknown underlying categorization forces: Shape, and Number)

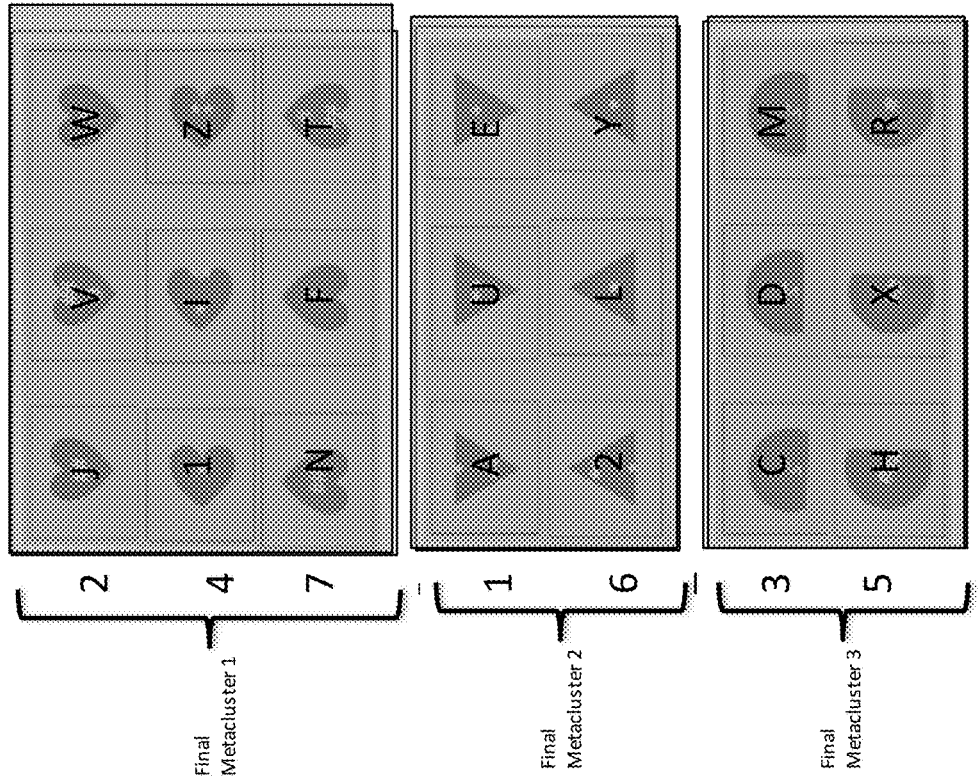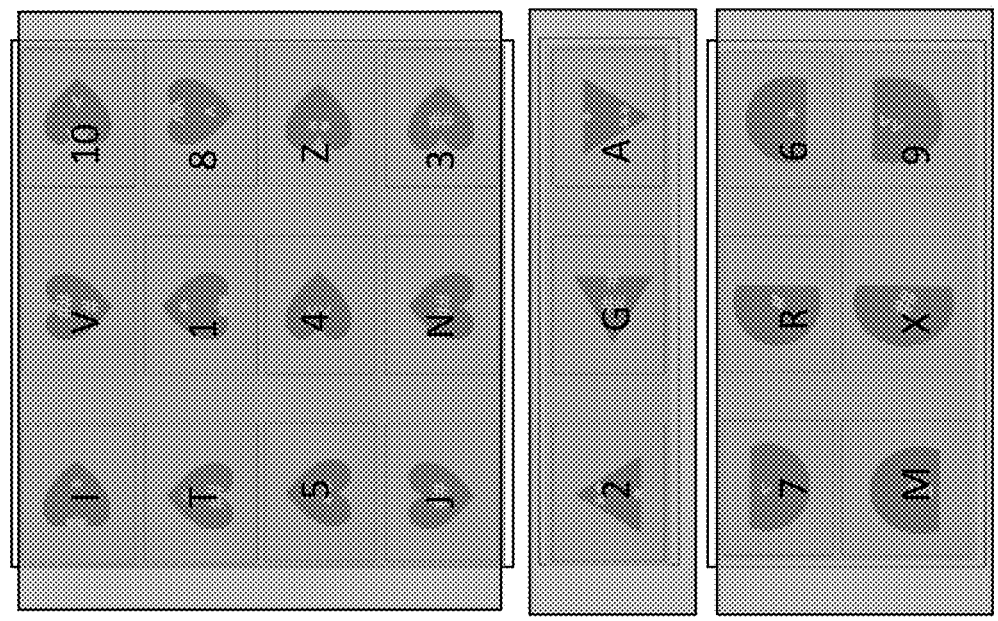
Fig. 4JJ

Fig. 4KK miRNA Disease Network

Instead of grouping by color it will group by Shape and Symbol:

(2 Unknown underlying categorization forces: Shape, and Symbol)

- Shape 1 Symbol 1
- Shape 2 Symbol 1
- Shape 3 Symbol 1
- Shape 1 Symbol 2
- Shape 2 Symbol 2
- Shape 3 Symbol 2
- Shape 1 Symbol 3
- Shape 2 Symbol 3
- Shape 3 Symbol 3

Gene Disease Network

(3 Unknown underlying categorization forces: Rotation, Shape, and Symbol)

- Shape 1 Symbol 1
- Shape 2 Symbol 1
- Shape 3 Symbol 1
- Shape 1 Symbol 2
- Shape 2 Symbol 2
- Shape 3 Symbol 2
- Shape 1 Symbol 3
- Shape 2 Symbol 3
- Shape 3 Symbol 3

Fig. 4LL

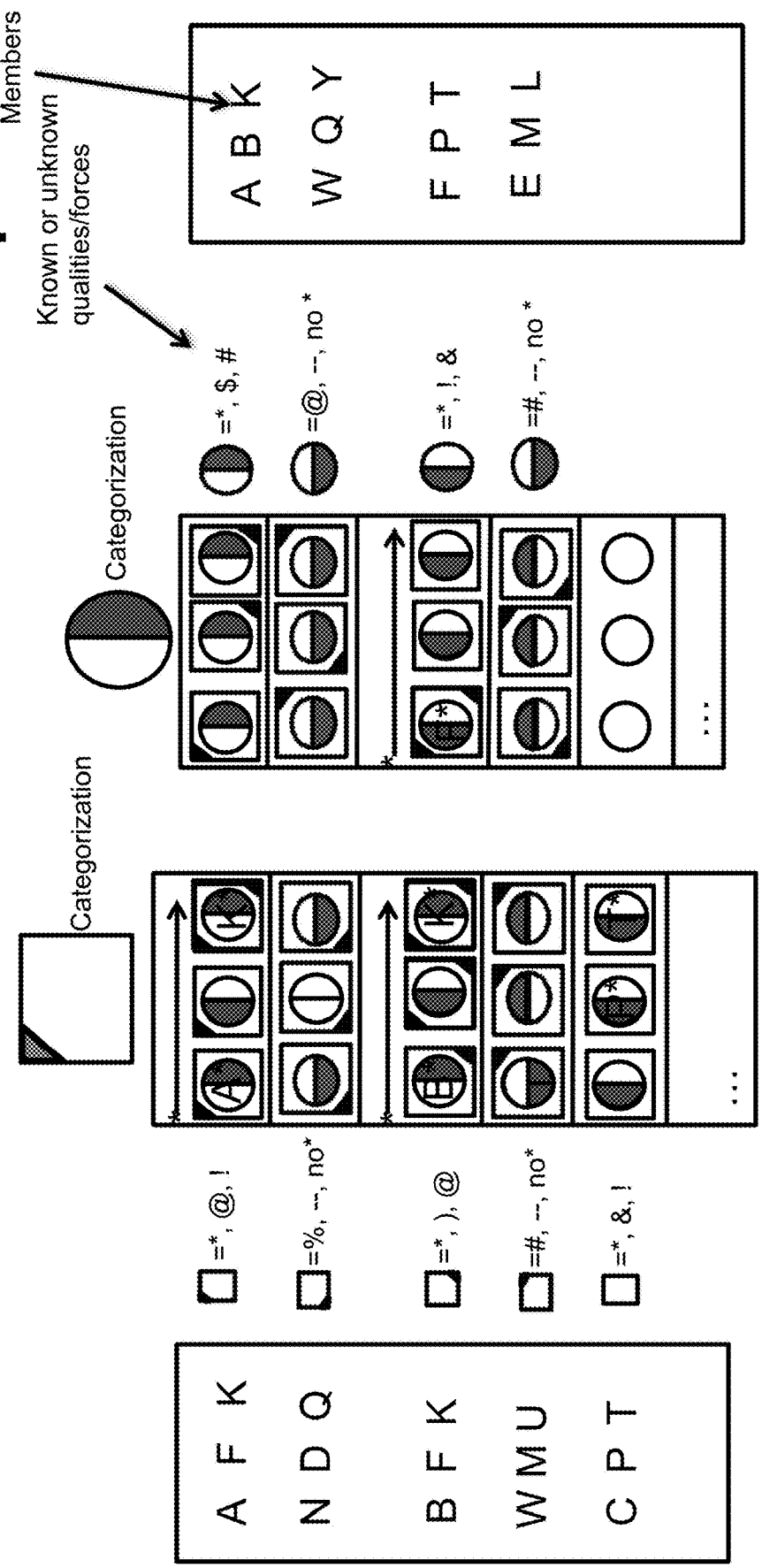

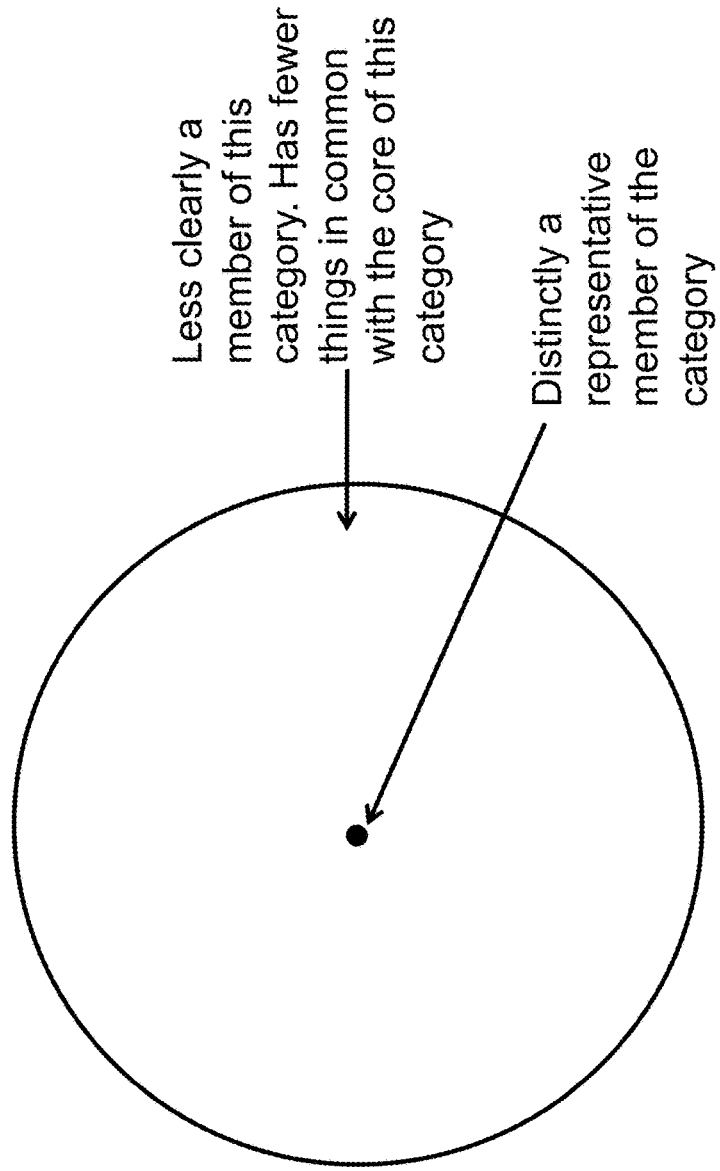

SYSTEMS AND METHODS FOR COMPARING NETWORKS, DETERMINING UNDERLYING FORCES BETWEEN THE NETWORKS, AND FORMING NEW METACLUSTERS WHEN SATURATION IS MET

PRIORITY DATA AND CROSS REFERENCE TO APPLICATION(S)

This application is a Non-provisional Patent Application receiving benefit from U.S. Provisional Patent Application Ser. No. 62/038,352, filed Aug. 17, 2014 and entitled "THE COMPREHENSION NORMALIZATION METHOD FOR BIOLOGICAL/NETWORK DATA", which is hereby incorporated by reference in its entirety. It is cross referenced, but does not claim priority, to U.S. Non-provisional patent application Ser. No. 14/154,151 filed Jan. 14, 2013/Jan. 13, 2014 Jan. 13, 2014 titled "COMPUTER TOOL FOR GROWING INFORMATION AND NORMALIZING COMPREHENSION OR COMPUTER TOOL FOR PERFORMING THE COMPREHENSION NORMALIZATION METHOD OF COMPARISON WITH DATA", which is also incorporated by reference in its entirety.

TECHNICAL FIELD OF THE DISCLOSURE

The disclosure relates generally to computer based research tools in big data research and, more particularly, to networks, comparative knowledge extraction and comprehension normalization. The disclosure relates further to a computer tool performing the Comprehension Normalization Method on network data. This method expands the Comprehension Normalization Method of languages into all other networks too, besides language, like social networks, economic networks, image data networks, biological networks, criminal networks, defense networks, advertising networks, etc. The present disclosure applies and expands the language Comprehension Normalization Method to work on all networks.

INTRODUCTORY CONCEPTS

Networks are a graphical representation, sometimes representing social connections, business connections, genetic connections etc. Networks have a scale free topology, meaning there is an asymmetry in the number of connections each node has, with a few nodes having a very large number and many nodes only having a few. The mathematics for networks is rather consistent across the different fields because of the theory of preferential attachment causing already very connected nodes to end up getting even more connected as new nodes are added to the network. Networks are helpful for finding modules/clusters, of nodes that have some things in common with each other causing them to be in the same cluster.

OVERVIEW

The present disclosure relates generally to using two networks, broken into clusters. The networks have the same nodes, but they are connected differently so the nodes within each clusters are different. It uses these two different sets of clusters, with the same nodes and different edge constructions/same members connected by different context, which results in clustering unique to each side, to find the underlying reasons for the clustering to take place, by using the underlying qualities underlying the grouping into clusters, and using the underlying qualities to group metaclusters of the starting clusters of each network, using the underlying qualities by proxy of the node membership in each cluster, to group the clusters by one or more of those underlying reasons/forces, so the researcher can discover those forces, and use clusters within that expanded metacluster, representative of those qualities of the force, to serve the same or similar purpose.

According to one embodiment, a computer-based tool implementing a Comprehension Normalization Method with networks enables exposure of the underlying forces, through using membership in a cluster as proxy for the force and groups by that force. The Comprehension Normalization Method is a computerized method that adds insight to network data.

The technical task performed by the computer-based tool performs the sort of comparison done by using underlying forces by proxy. In this patent I will use the term underlying forces, categorization factor, governance, rules, qualities, attributes, clusters, subnetwork, category, underlying reasons, values. Some of these mean similar things to each other, and are being used to communicate the same point in a slightly different vocabulary to potentially illustrate it better. Generally: Underlying force, or force, Underlying reason, or reason, Underlying Categorization Factor, or Categorization Factor, Government/governing forces, Type, All mean approximately the same thing. And: Quality, Quality affecting causation, Value, All mean approximately the same things. And: Cluster, Subnetwork, Category or subcategory, All mean approximately the same thing. And: Node, Member, Mean approximately the same thing. And: Edge Construction, Context and Form of Connection, All mean approximately the same thing.

I am using the words force and quality, similar to attribute and value, or metric and result under that metric, or rule/reason and aspect of that rule/reason. The end final metaclusters will be separated by the categorization force/attribute/metric/reason each metacluster having a different quality (of that force), or value (of that attribute), or result (of that metric). Each edge construction of a network can be driven by multiple underlying forces that are reasons for the categorization into clusters (categorization forces also literarily said as rules/reasons). If there are multiple that the original clusters have to satisfy different classifications, resulting in that if there are multiple forces, one clusters has multiple forces' qualities for it, but there are likely more than one cluster that has the same quality of the force for any one force because satisfying all of the forces to make the categorization permutated through the various qualities of the many forces. If one or more of the many forces (categorization forces) is in common between the two network edge constructions under comparison, then the resulting metaclusters will be grouped under that force in common into that force's particular qualities, where each metacluster will have a different quality (if multiple forces in common each metacluster will still have a different permutation of the qualities, but likely permutating through much fewer qualities), all qualities being of the same type, so one could say, there is a consistent quality (or set of quality) difference between each of the metaclusters, the consistent difference being qualities of the categorization force in common, the differences being that force's diversity of qualities/values/results under a metric.

BRIEF DESCRIPTION OF THE DRAWING

FIG. 2 is an example of the method showing the starting clusters

FIG. 3 is an example of the breakdown into metaclusters by the common underlying rule between the two starting networks.

FIG. 4A Is a simplified schematic diagram showing the underlying forces in large.

FIG. 4C is step 1 in a simplified idealized and unweighted schematic diagram illustrating an example running of the method with two networks.

FIG. 4D is step 2 in a simplified idealized and unweighted schematic diagram illustrating an example running of the method with two networks.

FIG. 4E is step 3 in a simplified idealized and unweighted schematic diagram illustrating an example running of the method with two networks.

FIG. 4F is step 4 in a simplified idealized and unweighted schematic diagram illustrating an example running of the method with two networks.

FIG. 4G is step 5 in a simplified idealized and unweighted schematic diagram illustrating an example running of the method with two networks.

FIG. 4I is step 7 in a simplified idealized and unweighted schematic diagram illustrating an example running of the method with two networks.

FIG. 4J is step 8 in a simplified idealized and unweighted schematic diagram illustrating an example running of the method with two networks.

FIG. 4K is a simplified idealized and unweighted schematic diagram illustrating saturation in an example running of the method with two networks.

FIG. 4L continues with beginning cluster 2, as a simplified idealized and unweighted schematic diagram illustrating an example running of the method with two comparative networks.

FIG. 4M is a simplified idealized and unweighted schematic diagram illustrating an example running of the method with two comparative networks.

FIG. 4N is a simplified idealized and unweighted schematic diagram illustrating an example running of the method with two comparative networks.

FIG. 4O is a simplified idealized and unweighted schematic diagram illustrating an example running of the method with two comparative networks.

FIG. 4P is a simplified idealized and unweighted schematic diagram illustrating an example running of the method with two comparative networks.

FIG. 4Q is a simplified idealized and unweighted schematic diagram illustrating an example running of the method with two comparative networks.

FIG. 4R is a simplified idealized and unweighted schematic diagram illustrating an example running of the method with two comparative networks.

FIG. 4S is a simplified idealized and unweighted schematic diagram illustrating an example running of the method with two comparative networks.

FIG. 4T is a simplified idealized and unweighted schematic diagram illustrating an example running of the method with two comparative networks.

FIG. 4U is a simplified idealized and unweighted schematic diagram illustrating an example running of the method with two comparative networks.

FIG. 4V is a simplified idealized and unweighted schematic diagram illustrating an example running of the method with two comparative networks.

FIG. 4W is a simplified idealized and unweighted schematic diagram illustrating an example running of the method with two comparative networks.

FIG. 4X is a simplified idealized and unweighted schematic diagram illustrating an example running of the method with two comparative networks.

FIG. 4Y is a simplified idealized so unweighted schematic diagram illustrating an example running of the method with two separate second comparative networks.

FIG. 4Z is a simplified idealized and unweighted schematic diagram illustrating an example running of the method with two comparative networks.

FIG. 4AA is a simplified idealized and unweighted schematic diagram illustrating an example running of the method with two comparative networks.

FIG. 4BB is a simplified idealized and unweighted schematic diagram illustrating an example running of the method with two comparative networks.

FIG. 4CC is a simplified idealized and unweighted schematic diagram illustrating an example running of the method with two comparative networks.

FIG. 4DD is a simplified idealized so unweighted schematic diagram illustrating an example running of the method with two separate second comparative networks.

FIG. 4EE is the starting clusters for one version of comparative network one and network two.

FIG. 4FF is a simplified schematic diagram illustrating the separation into metaclusters from the vantage of underlying forces.

FIG. 4GG is a simplified schematic diagram illustrating the division into metaclusters from the top level names of members in the clusters.

FIG. 4HH is a simplified schematic diagram illustrating the same primary network (network one) in comparison with a new network 2 that has shape as an underlying force in common.

FIG. 4II shows the simplified schematic diagram illustrating the division into metaclusters from the vantage of the underlying forces for the second comparison with network 1 and new network 2.

FIG. 4JJ is a simplified schematic diagram illustrating the division into metaclusters from the top level names of members in the clusters for the second comparison, new network 2

FIG. 4KK is a simplified schematic diagram illustrating what happens if there are 2 underlying forces in common between the two networks FIG. 4LL is a simplified schematic diagram illustrating comparing 3 networks at the same time.

FIG. 5 is a graph comparing the results of the Comprehension Normalization Method with a paper where the starting clusters were taken from.

FIG. 6 is a simplified schematic diagram illustrating another example of the underlying forces within a categorization.

FIG. 7 is a simplified schematic diagram displaying the difference between idealized membership and true membership.

DESCRIPTION OF EXAMPLE EMBODIMENTS OF THE DISCLOSURE

Rationale and Set Up for CNM

Figure 1:
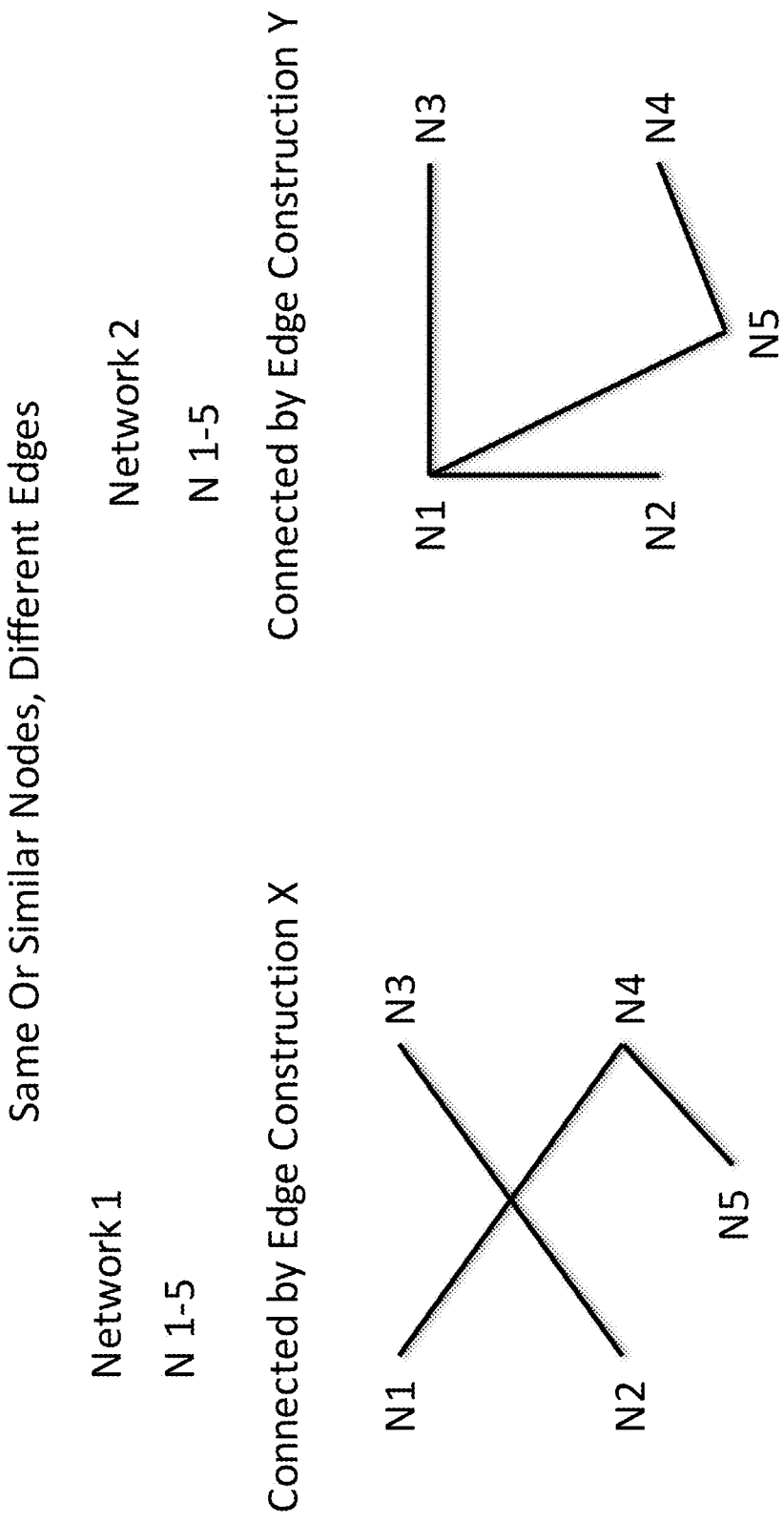
FIG. 1 is a simplified schematic diagram illustrating same nodes different edge constructions.

The Comprehension Normalization method is performed with beginning starting clusters. They can be small clusters like 2 diseases (and sometimes even only one) or they can be large like tens of thousands of people in one cluster. The number of clusters may be few, like 7 or may be large like hundreds or thousands. Clustering can be accomplished by many methods, to achieve these starting clusters, including hierarchical clustering, biclustering, multiview clustering, consensus clustering, hierarchical clustering with dynamic tree cutting, etc. The clustering can be done before or as part of the performance of the rest of the method. Our examples detailed start with clusters already created but other examples could require the software to do the clustering as part of the method before the rest can be completed. The initial clustering to get starting clusters from the unclustered data can be a step in the method, in some creations of software for the method.

In the Comprehension Normalization Method the clustering is usually done by two (or more) different edge constructions. Like one edge construction could be liver tissue genes connected if they are coexpressed in diabetic patients and another is liver tissue genes connected if they are coexpressed in obese patients. In this way the same thing, heart tissue, will be clustered two different ways. This can be called having a different edge construction, because the full title of the edge construction is different, or it can be called a different context, that is approximately the same. Many references to biological networks are used for real examples, but the Comprehension Normalization Method for Networks works for networks in all fields.

The method requires same or similar nodes/members. If not beginning as the same or similar, these nodes can be made to be similar through other methods, or can be more vaguely similar. The degree of similarity of the nodes/members in the two networks will effect the results, but the method assumes general similarity between the two data sets nodes in the clusters. The members of the clusters need to be generally similar nodes because the method and the rationale behind the metaclustering will be to use the member to represent something underneath, and to expand and assume the other data set has that something underneath. It can only use members to represent the same underlying force in the other network if there are some of the same or similar members in the two networks.

So same nodes, different edge constructions; two (or more) sets of clustering, two networks, or two categorizations. Clustering can be as simple as textually or otherwise, placing something into a separate category under a categorization. That will be assumed to be similar to clustering gotten by other methods. Clusters can look like categories, and clusters can look like subnetworks and clusters can look like a list of some sort of members in each cluster. Clusters could be something like chairs and tables and couches under the categorization furniture or clusters could be the set of genes names of genes coexpressed. These two sets of clusters are being called here as two networks even if the clusters are only subcategories. Different clustering techniques will cluster things differently. These different ways will change the starting clusters and possibly change the results. Clustering by two completely different ways would be similar to having two different edge constructions, the type of connection, thing connecting, is different.

Clusters have members, nodes in the cluster, and depending on the edge construction there are different underlying reasons for why a node is in one cluster and not another. These underlying reasons will be used by proxy of the members who are united in the cluster representing them, and thus the cluster with those members owning that quality are used to represent the underlying reasons/forces and the underlying reasons'/forces' different qualities. Forces have qualities for example, the categorization force of color could in one data set have the qualities of a cluster clustered by red, green, or blue. Those colors are the qualities of the unifying force, color. Other categorization forces have different qualities. When a network is made of multiple categorization forces clusters are some of the permutations with the qualities of the different forces, unfortunately. This convolutes things. If the network could be viewed by one force at a time, the different qualities of that force would be clusters grouped into metaclusters, and the metaclusters would be the range of qualities of that one force, which makes it easier to learn of the quality and the force, and get to use the same quality of that force, breaking (or really grouping clusters in) the same network into metaclusters of different forces. This method exposes one or more forces at a time, by limiting the forces by only grouping the metaclusters by the force in common between two edge constructions. This usually narrows the number of forces being permutated through significantly, and individual forces can start being evaluated.

Starting with two sets of clusters for the method, the two sets each have underlying forces and force qualities segregating and forming the clusters. Each side has a different set of forces, because an edge construction can be made up of many different forces. The sets of forces cause the original clustering under one edge construction to be clustering of (if there are multiple forces comprising the edge construction) to be permutations of all of the forces qualities. Different forces themselves are often not all grouped as one cluster of the edge construction's original clusters because two forces may group members into clusters differently, and the cluster's members has to satisfy multiple rules and rarely are all of the members of a quality for one rule in only one cluster.

The resulting metaclusters under different comparisons grouping it can be made of some of the same clusters as another comparison's set of metaclusters exposing a different independent force, but it will be a unique collection into the metacluster generally.

The Comprehension Normalization Method

Using two sets of clusters, the Comprehension Normalization Method works by accessing the qualities of those forces by proxy. First it uses the members of each of some/one of the clusters of Network A and looks for resonance of like membership enriched in some/one of the clusters in Network B. Resonance is the standard by which a large enough amount or percentage of the receiving cluster is similar to nodes in the sending cluster, that the receiving cluster should be considered an approximately a relevant match with the sending cluster. If the resonance function standard is reached and the receiving cluster is said to be an approximate match with the sending then the receiving cluster will be included in the metacluster of receiving clusters representing that particular sending cluster's qualities as the new intermediary representative cluster from the receiving side. The receiving side is now organized into new metaclusters and other clusters and the representative receiving metaclusters and other clusters of receiving side, become the sending clusters that receiving clusters in the first set must reach the standard of a large enough amount or percentage of the new receiving (or some other standard, like the requirements of different clustering methods as well as other functions that could serve as different standards the receiving cluster must meet to make a relevant match with the sending) but if the standard for resonance is met it counts as a match. Then the receiving network becomes the sending network, and the matches to the metaclusters and other clusters from the formerly receiving side are the new groups in the new sending's side and the new sending's side is now broken into representative metaclusters (representative of matching the previous sending metacluster) and other clusters. Iteratively the members used as proxies for the underlying forces, expands membership to suspected clusters back and forth and the resulting metaclusters, if there was a force in common, will be grouped by the membership clusters representative of the underlying qualities of that force. Sending the representative metaclusters and other clusters as the new sending is a pattern of representation back and forth can continue and in one instance until saturation. Saturation would be when repeating the pattern again returns the same metaclusters and clusters as the time before that.

The resonance function can be as total as the whole thing being similar to the sending is necessary for a match, or smaller than 1% similarity of the receiving is similar to anything in the sending to count the two sides as a match. Resonance can be numbers, any unit, or any percentages, or any possible method of considering threshold of similarity with the receiving cluster to the sending cluster, including even other clustering methods. The percentage/amount of the receiving cluster can be the percentage/amount or other rule, of a metacluster created by unification of the receiving network's clusters in a prior round.

The resonance function can be a changing variable changing with something like quantity of members or cycles of the iteration to increase or decrease in threshold. This can be automatic or not. The resonance function can be something like commuting membership only to the receiving cluster with the greatest number or highest percentage of members in common with the sending cluster. Also the resonance function can be a method. For example using any clustering method that would allow you to compare edge construction to edge construction imputing membership to the rest of the cluster, deemed by that method that is being used to establish sufficient membership of the receiving cluster to make a match. Alternate edge construction-to-edge construction resonance functions can be hierarchical clustering to establish membership qualities and impute membership, and other unspecified clustering methods as the different standards. The other clustering methods can be used a resonance function as different ways of standards imputing membership to the rest of the class or metacluster of the other network. The resonance function can be any way of setting a standard the receiving cluster must meet to match the sending cluster and be considered potentially representative of the underlying forces' qualities of the sending cluster including all ways of measuring proportions or setting atypical standards, like only allowing one match at a time, or two at a time or some unique clustering method, in addition to proportions and dynamic growing and shrinking types of standards of proportions. Clustering methods and an otherwise complex means of evaluating sufficient membership of the receiving side's clusters can be used as a resonance function as any form of standard to impute the membership.

The resonance function can be absolute, every single member counts as the full threshold for expanding membership to the rest of the cluster. To work without causing a domino effect, it is best if the resonance function (percentage based or otherwise measured by any method) is greater than the similarity between clusters of one network of either of the two networks.

More than two networks can be used. The Comprehension Normalization Method can be done with three networks or an unlimited number of networks, in cases with a lot of underlying rules in common. The Comprehension Normalization Method will find underlying rules in common between all three networks, or more. The multiple networks would all have similar nodes but 3 or more different edge constructions.

What the resonance function is (the chosen standard), can be something determined or set at automatically or not automatically based on an evaluation of the overlap between cluster membership in one network, in each network. It can be chosen based on the field it is being applied on. It might be many standards run at the same time, to figure out the best resonance function based on the character of the results by the different levels, percentages, values, increasing or decreasing values, methods etc.

In brief, the Comprehension Normalization Method uses membership in two networks where the same or similar members are organized differently (i.e. same or similar nodes under a different edge construction/different forms of connection/different contexts). The other way of organizing the first network's members into members of the second network's clusters will organize the members differently. Because they are organized differently members comprising a single cluster on one side might be spread across multiple clusters on the other side and vice versa. Members activate underlying forces, qualities affecting causation. If there is a quality, both true to the clustering of one network, and the membership organization (i.e. clustering) of the other, meaning in both data sets that same quality is true for the whole cluster, then even though the clusters have different members, all of the members of a cluster represent that quality. This means the unique cluster members that one side has and not the other, share the same quality with the other cluster members' quality, and membership of the quality, while still unknown, should be spread to those members too. Iteratively this eventually spreads membership of the quality to all of the quality's clusters for both data sets, and the membership of the unknown quality from both sets unites clusters that have the same unknown quality with each other from the original single set. The method accesses the quality in common between two edge constructions by proxy and groups clusters in the original set and the other set by that quality in common. It uses two networks that are different, and it uses their members to access the causal relationships by proxy of the members, to group the clusters by the quality affecting causation in the same way. This method using two edge constructions makes that research fast, and will help researchers in all fields find qualities affecting causation and group by those qualities.

Science-Worked Example

FIG. 1 is a Figure displaying similar nodes with different edge constructions. A separate edge construction could be connecting by hair color and a second one connecting by eye color on the same or similar population. Or one connecting by diseases sharing an implicated gene and another set of diseases connected if they share adjacent metabolic reactions.

FIG. 2 shows and example of a school district's population. One of the edge constructions is grouping by friend social cliques, and the other edge construction is grouping by school sports teams.

FIG. 3 shows a grouping by one of the forces in common between the two break downs, that force being schools within the district. This shows taking something comprised of many elements—there are a number of reasons for why a child would be in one social clique and not another and simplifying it to one or a few elements, that element left over being the break down of schools which has to do with social cliques and sports teams.

FIG. 4 A, is a larger Figure of the two networks that will be used for A-MM so details can be seen. In these two networks, the first is a network with three underlying forces, rotation, shape, and symbol. The second is a network with two underlying forces, rotation and number. Rotation has values up, down, and sideways. Shape has values, triangle, heart, half circle. Symbol has values, #, *, ^. Number has values 1, 2, or 3 symbols. If you see, every row of network one (the network on the right) has the same rotation row wide, shape row wide, and symbol row wide. The first row has rotation down, shape triangle, symbol * and a diversity of numbers—from the right, 1, 2, and 3. The second network (the network on the left) every row of the network has the same rotation and number. The first row has rotation down, and number of symbol repetition 3. It has symbols from the right of ^^^, ^^^, ***. And it is shape half circle, triangle, triangle.

For each of the rows of Network 1 (network on the right from the right to the left).
Row 1: shape, triangle, rotation, down, symbol *, number *, , *
Row 2: Heart, up, #, ###, ##.
Row 3: Half Circle, down, ^^, ^^, ^^
Row 4: heart, sideways, , *, *
Row 5, half circle, sideways, #, ##, ###.
Row 6: triangle, up, *, *, ***
Row 7: Heart, down, ###, #, ##.

For each of the rows of Network 2 (left network, from right to left)
Row 1: half circle, triangle, triangle, down, ^^^, ^^^, ***
Row 2: heart, triangle, half circle, down, #, *, ^
Row 3: heart, half circle, triangle, sideways, ***, ###, ###.
Row 4: Triangle, half circle, heart, up, **, ##, ##.
Row 5: half circle, heart, half circle, down, **, ##, ^^
Row 6: half circle, heart, half circle, sideways, #, #, *
Row 7: heart, triangle, half circle, down, ###, ###, ^^^

These are the underlying qualities of the underlying forces rotation, shape, symbol, and number. Usually these are not known ahead of time. Note that if a complete population were perfectly clustered the rows of each network would be permutations of the 3 elements by each permutation of qualities, and the 2 elements by each permutation of qualities.

Figure 4B:
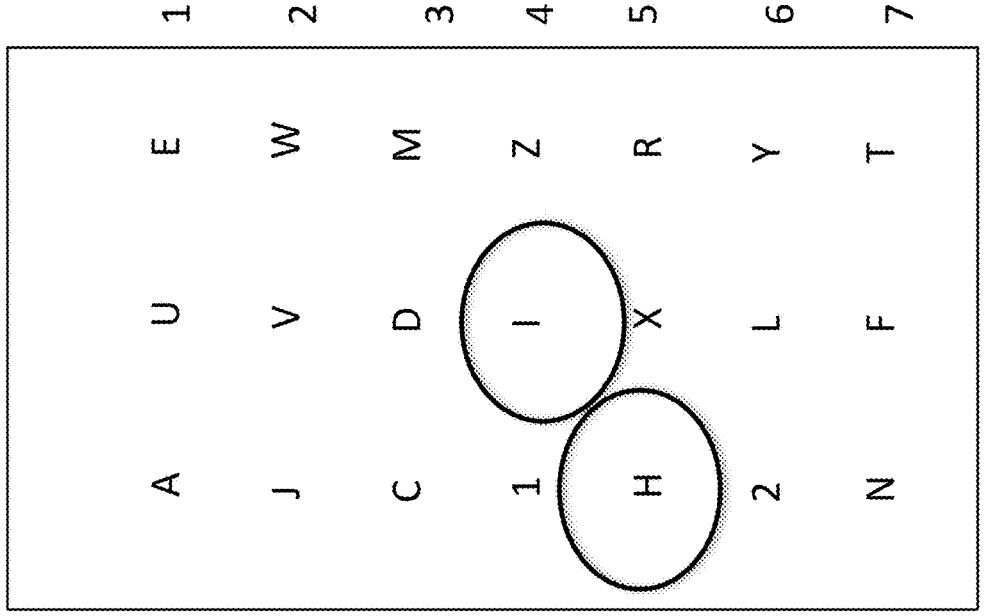
FIG. 4B is a simplified schematic diagram illustrating the top layer of the named contents in the clusters.

FIG. 4B shows what you would see of the two networks—imaginary Gene Disease Network, and imaginary Metabolic Disease Network. There are letters and numbers (which signify diseases, there is a key to the letters on the right). These diseases in each cluster are all that are known of the two networks of the example (more can be known in another embodiment but for this example of the method is not necessary). So the researcher sees diseases A, U, E as cluster one instead of the forces and qualities governing the collection of diseases into cluster one and while diseases are what are known, organizing by those qualities to find the underlying forces is what the method does grouping the other elements permutations of the qualities, into one if there is only one remaining element left over to group by. The different comparisons grouping by different elements' qualities and grouping differently to reveal the expanded membership of each underlying forces qualities in order to see the forces and use the expanded membership of a quality that they want to use.

FIGS. 4C-4CC as separate views:

FIG. 4C begins the iteration of the method demonstrated starting with cluster one's members A, U, and E, which as idealized members are all weighted here the same. (It is implied in this idealized example with perfect membership (all members in a cluster share all membership qualities with everyone else in the cluster), that here the resonance function (can be automatically "every" or automatically anything without choosing) chosen is chosen at 1, every single member counts for the qualities. FIG. 4C-4LL shows the iterative back and forth of expanding membership by member representation in a cluster.

FIG. 4D Because this is an idealized network A, U, and E fully represent cluster one, but as shown in FIG. 7, a non-idealized network will have some members that are more representative than others, and those towards the center of FIG. 7 that represent the cluster more are weighted as more valuable. Here the contents of the cluster one look for similar membership in the second network. In the second network, clusters one and two house members A and E and because this is an idealized network, that is enough here to expand membership based on those single members to the whole class of clusters 1 and 2.

FIG. 4E shows that in the clusters with sufficient membership representation (it can be a percentage of the receiving cluster or a percentage of the weighted membership of the sending cluster in the receiving cluster (also weighted but not here because it is idealized). Once sufficient representative membership is shown as a proportion of the receiving cluster, the chosen clusters are combined. These become the new sending metaclusters. For cluster 1 of network one, combined clusters 1 and 2 are the new representative of cluster one, which for convenience here can be called cluster 1 prime. The combined clusters create the new representative membership. Again here is idealized so every member counts as the full representative, where as in other embodiments, A, B, C, D, E, F may represent the underlying forces of the cluster more or less than each other, as shown by information in the original clustering, like the correlation matrix, etc. A, B, C, D, E, F are the new representative members of cluster 1 (network 1).

FIG. 4F shows that these members, or the sending metacluster, looks for similar cluster membership in the receiving clusters—now network 1 is the receiving network. The sending metacluster of the combined 1 and 2 of network 2 find similar (representative proportion) membership in clusters 1, 3, and 7 (network 1) with A, E; C, D; F. This representative membership in the receiving clusters means that the representation of the underlying qualities can be attributed to the rest of the cluster, and the new membership representing Cluster 1 is A, U, E, C, D, M, N, F, T.

FIG. 4G shows, again these are combined into the new sending metacluster, representing original cluster 1, called here cluster 1 prime and including network 1's cluster 1, 3, and 7—these are all combined as sending metacluster 1".

Figure 4H:
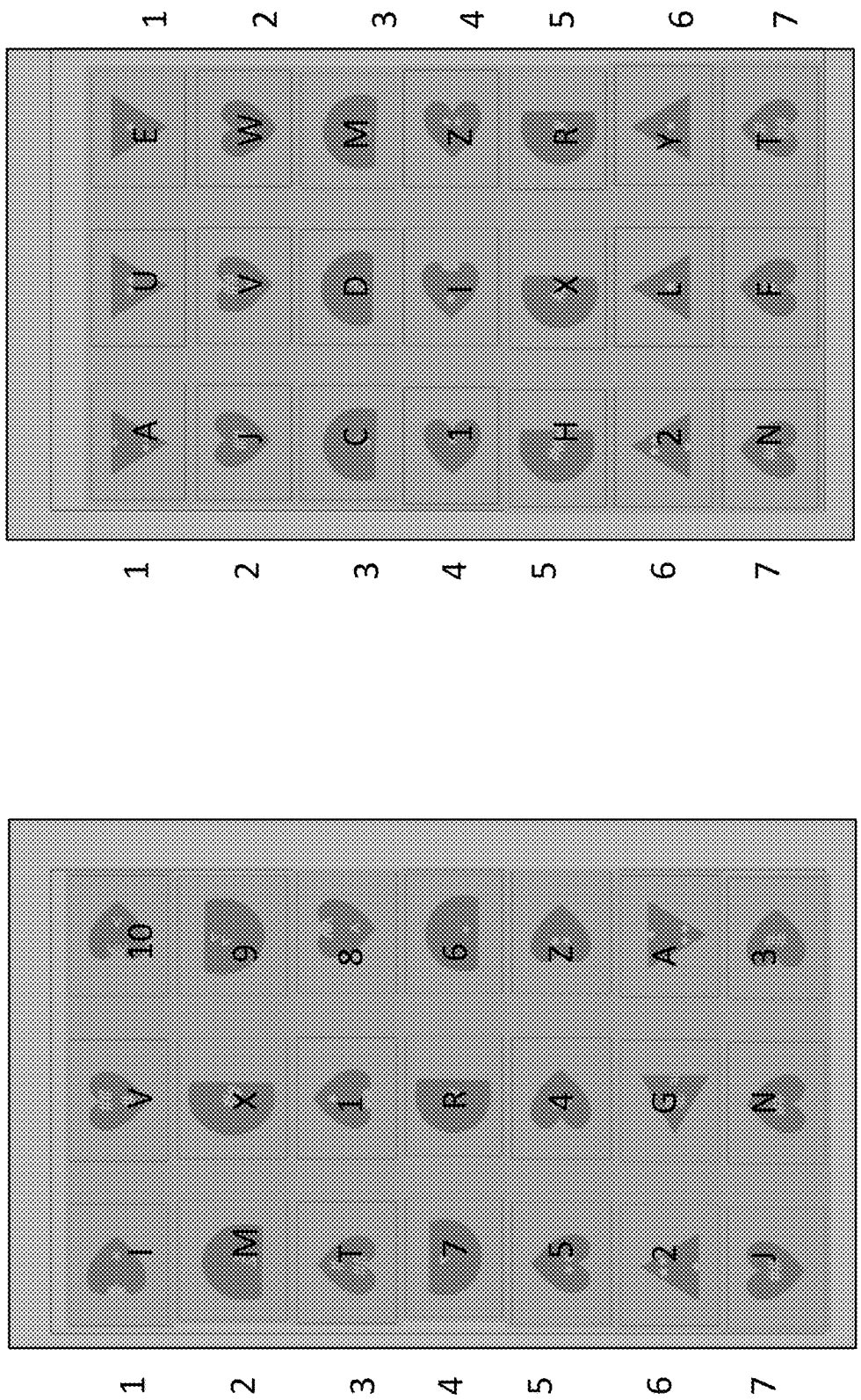
FIG. 4H is step 6 in a simplified idealized and unweighted schematic diagram illustrating an example running of the method with two networks.

FIG. 4H shows, the new sending meta cluster looks for representative membership in each of the original receiving clusters. Representative can be measured many ways. This time it finds representative membership in clusters 1, 2, 5, and 7 of network 2.

FIG. 4I shows, once again, the receiving clusters with sufficient representative membership are combined into the new sending metacluster. This become the new cluster representing original cluster 1 called here cluster 1'''.

FIG. 4J shows representative membership is found in clusters 1, 3, and 7 of network 1. Because 1, 3, and 7 were already the representative clusters of network 1's cluster 1, when it combines and looks for membership on the other side, it will find the same clusters here in this idealized network.

FIG. 4K shows, when it stops changing, adding or subtracting clusters (it can subtract in another embodiment because of things like an increasing resonance function, though often there are not enough clusters to support enough rounds to have an increasing resonance function) then we call it saturation, and the iterative method representing cluster 1 ceases to continue, and network 1's cluster 1, 3 and 7, are the representative of cluster 1. Ultimately, in this idealized network, cluster 3 will also find it is represented by clusters 1, 3, and 7, as well as 7 finding that. In a current prototype of the method, it says, cluster 1 representation is similar to cluster 3, and cluster 7. Clusters 1, 3, and 7 are then combined as metacluster 1.

FIG. 4L shows that often, the software would be designed so that all the starting clusters from one network can search for membership in the receiving clusters at the same time.

FIG. 4M shows the iterative method beginning with network 1 cluster 2—with fully representative members all weighed identically, J, V, and W.

FIG. 4N shows, fully representative member J is also represented in network 2 cluster 4. Membership representing network 1 cluster 2 qualities (of the underlying forces in common between networks one and two) is expanded to the rest of the class of cluster 4 and J, K, and L become representative of the overlapping underlying quality of cluster 2 network 1.

FIG. 4O shows J, K, and L are now representative cluster 2'''.

FIG. 4P shows as the iterative method continues, it finds representative membership in network 1 clusters 2 and 6.

FIG. 4Q shows network 1 clusters 2 and 6 are combined as new sending metacluster 2''' and representative membership is expanded here (equally because it is idealized, in other embodiments it can be unequal based in part of qualities like those shown in FIG. 7 about some members being more representative than others) to the rest of the class of clusters 2 and 6 which are now combined into the sending metacluster.

FIG. 4R shows the iteration continues and finds representative membership in cluster 4 again, and only cluster 4. Because it has found the same cluster, in this embodiment, that means if it were sent back it would find the same clusters 2 and 6 and thus the membership of the representative metacluster has stopped changing, (adding or subtracting).

FIG. 4S shows cluster 2's representative metaclusters have reached saturation, and the iteration for cluster 2 stops.

FIG. 4T shows that it is possible if desired to also run the iterative method beginning with network 1 cluster 4 at the same time.

FIG. 4U shows cluster 4 starts out with perfectly representative members 1, I and Z.

FIG. 4V shows 1, I, and Z find representative membership in network 2's cluster 3.

FIG. 4W shows the representation of the underlying force(s) in common between the two networks expands to the rest of cluster 3.

FIG. 4X shows looking for representative membership (like a sufficient proportion of each individual original clusters as the receiving clusters) and finds that in receiving cluster 4 and 5.

FIG. 4Y shows receiving clusters 4 and 5 are combined into the new sending metacluster, which seeks to find overlap in representative membership in each of the original receiving clusters in network 2.

FIG. 4Z shows it finds representative membership in clusters 3 and 6 of network 2. The resonance function is what determines if there is representative membership in the receiving cluster. There can be a lot of variation and complexity to designing the resonance function, but ultimately it is looking for resonance i.e. sufficient representation of membership in the receiving cluster.

FIG. 4AA shows the receiving clusters with sufficient representative membership are combined as the new representative sending metacluster 4'''.

FIG. 4BB The sending metacluster made of network 2's cluster 3, and 6, looks for sufficient representative membership in cluster of network 1.

FIG. 4CC shows the sending metacluster of network 2's clusters 3 and 6 finds resonance with the same receiving clusters 4 and 5, and thus in this idealized embodiment, that means saturation has been met and because the sending metacluster is no longer changing in membership.

Descriptions of the several views within FIG. 4 at the same time:

(FIG. 4C-4CC); while usually all of the starting clusters from network one can often look for resonance at the same time, the example illustrates the clusters explored separately. In the example it begins with the members in cluster one. The members in cluster one represent certain qualities of the forces. If these forces are true for both networks, than the other members in the cluster will have the same qualities of the force in common as the original members from the other side have. Cluster one begins with cluster members A, U and E and looks for clusters in the second network housing A, U, or E, because if there is a force in common, the clusters in the other set with those members should all have the same quality as the incoming member's quality for that force. In network 2, rows 1, and 2 have A and E in them. All of 1 and all of 2 are now considered representers of that underlying quality. So A, B, C, and D, E, F are combined into one new cluster, that now as an enlarged cluster are all of the members representing this quality. The enlarged network two reciprocal network 1 cluster 1 cluster of ABCDEF representative members are housed in clusters 1, 3, and 7 of network 1. The rest of the cluster's letters in the same cluster as C and F etc, are representative of this quality that members in the second network's reciprocal cluster of network one's original cluster represent. AUECDMNFT are all grouped into a new cluster, representing the quality (ies) (or the force/forces in common) underlying original cluster 1. AUECDMNFT are found in cluster 1, 2, 5, and 7 of network two. The four clusters are combined and all four clusters represent the quality of original network 1 cluster 1. When this is sent back over, if finds only the same 3 clusters of network one again. If the back and fourth were to continue now the clusters would not change. We call this saturation. The back and fourth from cluster one is complete.

If beginning with cluster 3, it would also have clusters 1, 3, and 7 in its final cluster. And beginning with cluster 7 would also have clusters 1, 3, and 7. That means those three clusters make up a metacluster, metacluster one.

Beginning with cluster two, the same iterative back and forth expanding membership is conducted, resulting in clusters 2 and 6 as metacluster 2 for network one and clusters 4 as metacluster 2 of network 2. Beginning with cluster 4, ends up grouping starting clusters 4 and 5 of network one into metacluster 3 and 3 and 6 of network 2 into metacluster 3, at the iterative until saturation beginning from cluster 4.

In this very simplified idealized network with only 7 clusters (there can be a different number of starting clusters on each side) in both networks only breaks into 3 final metaclusters. If there was an underlying force in common between network 1 and network 2, then the three metaclusters will be broken down by the qualities of that force (or permutations of qualities of the remaining forces). Here underneath our diseases A, B, C etc. network A was grouped into rows by the unifying force of rotation, shape and symbol and network B was grouped into clusters by the unifying force of rotation and number. Rotation is a force in common. So the final 3 metaclusters will be the 3 qualities, the range, of force rotation, i.e. up, down and sideways and the three metaclusters, metacluster wide will be either up, down or sideways. Here because there was only one force in common the final metacluster includes all clusters with that rotation's quality in one final metacluster.

FIG. 4DD shows that the two networks, after running CNM, will cluster into metaclusters, by the underlying force(s) in common between the two networks, if there are any.

FIG. 4EE shows the beginning disease letters overlaying the underlying qualities the letters stand as proxy to.

FIG. 4FF show the final break down underneath the letters, that the letters mean underneath. Here metacluster one is rotated down, metacluster 2 up and metacluster 3 sideways.

FIG. 4GG shows the letters the researcher would see as the result, but the letters grouped by these underlying qualities that have been guiding the grouping underneath using the letters as proxy. AUECDMNFT all represent the same underlying quality of down in the force rotation.

FIG. 4HH shows what happens if the same starting network, network 1 is compared to a different network 2, here a network two organized into clusters by the forces of shape and number. Again the researcher sees only the letters, which represent the unknown qualities of the forces underneath.

FIG. 4II shows that because the force of shape was in common this time, the metaclusters are clusters of hearts, triangles, and half circles.

FIG. 4JJ shows the letters on top grouped by the underlying quality underneath, the letters now grouped would be what the researcher sees as the final results.

FIG. 4KK shows that if multiple forces are left in common between the two networks, then the results will be (some) permutations still, but only permutate through the qualities of the remaining forces in common. Here with 2 forces in common each with 3 qualities, then instead of 3 resulting metaclusters there will be 9, each three qualities for each of the other's 3 qualities. Performing CNM using the final metaclusters as starting clusters against a $3^{rd}$ network could reduce the permutations back down to only one left if there is only one force left in common between the final metaclusters and network 3. Here the two forces in common are Shape and Symbol and there are 9 in the permutation of the 3 shapes and 3 symbols with each other. There can be any number in common, it depends on the data, and it will result in permutations to the extent that the data is a complete representation of the variability of the network, in complete networks may only have some of the permutation, but even when it is only some, the final metacluster will have 2 (or more if more forces) forces let uniting the nodes in those metaclusters.

FIG. 4LL shows 3 Networks with a total of one thing in common across the 3, only shape is in all three, so performing the Comprehension Normalization Method with three, through two have two forces in common, only one force is left in common in all three and that is the one force the final metaclusters are broken down by. There can be any number of networks included, but it will have this effect of finding only the forces in common with the whole set.

Figure 5:
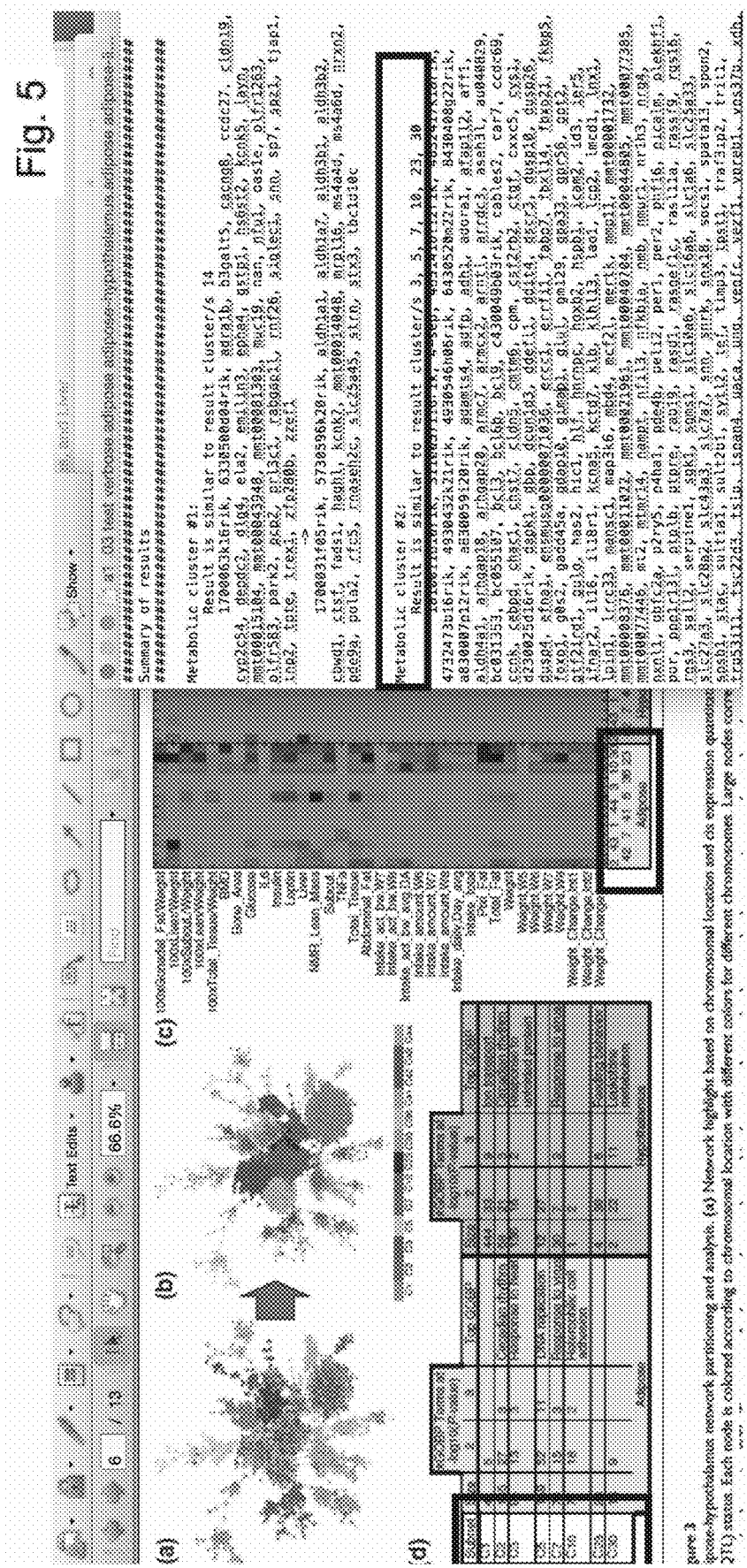

FIG. 5 is the data and comparison from the example use of our method with data from the paper titled "Multi-tissue coexpression networks reveal unexpected subnetworks associated with disease". Data from a sample of obese mice, we used the tissue-to-tissue data and single tissue coexpression data and with the two tissue results from the coexpression, slit apart as two separate data sets with nodes that were one tissue's or the other's we extract 9 data sets. Adipose nodes from Adipose single tissue coexpression, adipose nodes with adipose-liver coexpression, and adipose from adipose hypothalamus coexpression [the example that goes with this figure is from the adipose-hypothalamus coexpression, seen in that heatmap, and seen in our with results with the comparative secondary network, adipose nodes from adipose-liver coexpression]. Also liver nodes with liver single tissue gene coexpression, and liver nodes with bipartite liver-adipose coexpression, and liver nodes from liver-hypothalamus coexpression, then hypothalamus nodes with hypothalamus single tissue gene coexpression, and Hypothalamus nodes from hypothalamus-adipose coexpression, and hypothalamus nodes from hypothalamus-liver coexpression. 9 data sets. Only six of them were from bi-tissue coespression. We did all of the 72 possible combinations with the 9 data sets, but the only supposedly actual ones, were the ones that were used with the same nodes on both sides of the comparison, and secondly, were the 6 of the three nodes 2 tissue coexpression that were cross tissue coexpression, and so each set of nodes only had 2 data sets that could be compared with each other with the same nodes, and this resulted in doing the comparison between the two (like adipose-liver v adipose-hypothalamus) and then also doing the reciprocal, (starting with adipose-hypothalamus nodes as the primary lead data set and compared against the adipose-liver as the secondary data set). Accordingly we received 6 sets of metaclusters, clustering the clusters from the adipose-liver into meta clusters and when the reciprocal, clustering the clusters from adipose-hypothalamus. We received six sets of clusters. Clusters from starting from each of the two sides of clusters from the 3 tissues. Our only starting material was the gene names clustered by the three tissue to tissue coexpressions. We did not have to know what the eQTLs were or which clusters were enriched for one type of eQTL or the other (trans or cis). We only had to know the gene names to create the metaclusters with this Comprehension Normalization Method. After our 6 comparisons, our six sets of metaclusters (the metaclusters being clusters from each starting clusters). The results are:

Adipose nodes, Adipose-Hypothalamus clusters with Adipose-liver. Resonance function 3%: (metacluster from clusters—(2, 3, 5, 7, 10, 23, 30), (16, 29, 37), (18, 24, 31), (1, 14), (11, 15), (13, 39). Resonance function 5% (a more strict standard because for a match it requires that 5% of the receiving cluster has to be in the sending metacluster vs 3%): (2, 5, 10, 23, 30), (16, 37), (18, 31), (1, 14), (13, 3).

Adipose nodes, Adipose-Liver clusters with Adipose-Hypothalamus: Resonance function 3%: (1, 2, 3, 4, 5, 11), (7, 28, 35), (18, 20, 31), (19, 23, 50)(21, 40, 41), (16, 38), (44, 57). Resonance function 5%: (1, 2, 5, 11), (7, 28, 35), (20, 31), (23, 50), (21, 40), (44, 57).

The rest of the results showed the clusters from the other 4 cluster starting sets.

These results are special because the only large cluster, the 2, 3, 5, 7, 10, 23, and 30 are 7 out of 8 in the type two clusters with larger than 10 genes, from the paper we used the data from, without needing to know the eQTLs and only starting with plain gene names in clusters. So it clustered a group that did have something in common. This set of seven are also the 7 most correlated to the changes in the mouse obesity traits measured. And more specifically, our higher standard, narrowed the resulting clusters that were correlated even more to the mouse obesity traits. The one cluster we did not pick up, cluster 1 has very little correlation to changes in the mouse obesity phenotypes. We have not yet reviewed if there are other underlying things uniting the other smaller clusters too. The type to subnetwork of clusters are clusters all enriched for trans-eQTLs and not cis_eQTLs. The heatmap shows the clusters on the bottom and the obesity traits on the left side, the red showing up in black and white as the darker grey and the green as lighter grey. The red means low p-value and the green means a p-value of 1. The large metacluster has all of the clusters which on the bottom show up on the graph with low p-value in correlation to the traits. So this method was able to find the type-2 subnetwork which is most correlated to these obesity traits, without knowing where the eQTLs where, which were cis and trans, which clusters were enriched for them. All of these which in another field where the eQTLs equivalent quality is not known (it was hard and took many hours and computing power to be able to identify eQTLs and eQTL hotspots), then only with our method which requires almost no prior knowledge in the field besides the data, and can find this special group as metaclusters.

FIG. 6 Logic:

The first skimming has a little bit of review in it, but the idealized example is from a slightly different perspective. Instead of using the words 'language' or 'network', I am going to look at it from the perspective of 'category types'. So instead of discussing how we are using 'rules' in a language or 'co-governance', we are going to be discussing how we are using 'qualities' of, 'variables' of, 'forces' on, or 'elements' to members of a sub-category. And instead of using the words 'sub-network', I will describe it as a 'subcategory' or 'cluster' or 'class'. I will show this perspective with an idealized example. Members united into a category share a certain set of qualities. In the idealized example all members of the sub-category are perfect members, class-wide all members share all membership qualities.

With two categorizations, if there is a quality that is a decisive aspect of the categorization, something a dividing force will act on in both categorizations, then the presence of that quality in either data set is class-wide and letting the presence of one member imbue representation status to the rest of its class correctly picks up more instances of categories with that quality in the other data set [in the ensuing rounds of CNM]. The Comprehension Normalization Method works by extending membership in one category, representing certain qualities, to the other side's categories that share sufficient amount of the same or similar members. If there is an overlap in one or more of the categorization forces, then extending membership to the whole of a sub-category containing a representative member, will extend membership of that quality appropriately.

The categorization imposes forces/categorization factors across the data, and the data have different qualities the force is reacting to when dividing. If there is an overlap in one of the underlying categorization reasons between the two data sets' categorizations, then this method will organize the starting categories for each data set into bigger categories hosting bigger category wide uniformity only for the factor in common. When the Comprehension Normalization Method extends membership owning that discriminating quality to the rest of the category/class that harbors a substantial amount of members that are representative of that decisive quality, then the back and forth extending class-wide like this will eventually get most instances of the shared quality's presence and unite the categories within each categorization. Membership in all of the extended categories is representative membership of the categorization factor in common, and instances of the extended membership in all categories on the first side, will identify all of the categories in the first that also contain the quality of the factor in common. This will highlight that discriminating quality's presence, even when we didn't know what that overlapped force was. If the two categorizations actually have some of those discriminating forces in common, then we can start to see the influence of that quality, separate from the other qualities of the class. When the same original data set is compared with a different categorization, then if they have different categorization forces in common, then the extending of membership indentifies instances of the new categorization factor in common's qualities.

In FIG. 5 the idealized example you start with two different categorizations. On one side the categorization is of square variation, and using a lot of the same data, on the other side the categorization is the variations of the circle. Like when we were using languages and the members drawn together were proxies for the rule, in the example, the first red half-circle category is represented by members A, B and K. There are forces responding to qualities the members of a class have. The forces are categorization-wide and the qualities are class-wide. Let's say the half circle has 10 (unknown) qualities relevant to one of this categorization division's forces. A couple are shown. And on the other side there are 10 (unknown) discriminable qualities relevant to one of the square category division's forces. Again some are shown (for our benefit, even though they may be unknown). If the two sides actually have some of those categorization-wide forces in common, then the Comprehension Normalization Method can let you see a new breakdown by that force into a spread of qualities. There is a force that is a component of every category of the categorization, and so co-governance is when that sort of fundamental force is in both categorizations, the same one. At the end you will have two divisions for each quality, those in the meta-category and those outside of the meta-category. These two divisions were described by the force in common between the two categorizations, (if there is at least one such force), which that starting cluster has. And looking at the cluster from totally different categorizations (e.g. by hearts) will regroup the entire starting categorization's clusters by different shared forces, highlighting different things in the data. We start with this first sub-category/class of the red half circles (whose members are A, B, and K) and look for that red half circle's members in the blue. Because the two categorization types share a quality which is a categorization factor i.e. class-wide, (which last time I called co-government) that shared quality means every member in a class harboring this red half circle's member, must have the common, shared quality class-wide. Here the quality star (quality of the force in common) is a component of the categorization for both categorizations and there is natural co-governance in which case the results are meaningful.

If A and K are included and A and K happen to have a quality that is also necessary to blue's divisions, then because the quality is class-wide and the whole blue division has the quality with the red member A, F bears this quality. By the presence of F this quality is invoked in a whole class in which F is present, when it returns to finding resonant membership in the red circles. The rules and rule's aspects (or the qualities) are codified by the proxy of who's a member. Members of the class are proxies for the rule's qualities regulating this category class-wide. These qualities about the class that differentiates the class and is part of the relationship of that class to the other classes that are under the same categorization. The united meta-cluster of circle subtypes 1, and 3 are united to each other because of the membership of both blue's relevant additional members and red's relevant additional members (expanding it to blue class-wide). The resulting combined part all share the category determinative quality. Because this is a miniaturized simplified example, it only went back and forth a few times and is now at saturation. In later examples today worked out I will show you more complexity behind it. Because of the two categorization types and Comprehension Normalization Method, you can measure and divide by a force you didn't even know about before. If there were a shared decisive quality then it will pick up most instances of the shared quality and that shared quality will be in the meta-class and not in the rest.

FIG. 7 For real life, category membership is not black and white. Instead there will be qualities that are generally/usually necessary to membership, but not always represented by every member. You get members of the category with a lot of variables that overlap, but even vital variables do not overlap in all members, so when you want to use these members as representative of qualities that truly represent the class, a more substantial quantity of members would be required for it to be assumed that the members represent that class on the vital details. Because in real life, and especially with larger and larger, higher order clusters, not all members have the same quality, nor do all members represent the key qualities of the category equally. This is just a consequence of high order categorization (involving a extremely large number of variables). As a result, a resonance which then expands the quality to the whole class is not granted unless a very representative portion of the category (maybe half the members) resonate, then resonance and its resulting extending of the quality across a resonating class is represented to be meaningfully representative of the class and is granted. With enough data, enough people, enough representative members the method can be used on population averages, and working with averages, the idealized conditions are close to true again.

The question about prior information and that the researcher seems to be ceding to prior information is true. The Comprehension Normalization Method's results rely on prior information and will only have answers as good as the current up to date information. Where the categorical divisions come from is from already determined currently divided categories. If instead of using network clustering methods to form clusters, a lab wants to use unstructured data, the horizontal algorithm finds instances through unstructured data, of categorization, but already determined, and uses the threshold of those results as the categories. It never tries to categorize anything based on its own calculations but finds instances where annotations describing a categorization exist. The categorization can also be taken from elements of a graph. In a later example we have worked out for you we took data from two networks (published in papers) made from the data from OMIM database and KEGG and BiGG database annotations on relationships that genes, diseases, and metabolic pathways which have been recognized by researchers as of when the papers were written that extracted the information from those databases. Different methods for creating clusters, (like dynamic tree cutting of a hierarchical clustering), and of designating a category title to that cluster (like calling one group of clusters a disease module or function module because it is enriched for genes related to a specific function or disease), are prior information choices made by the researcher that make the results meaningful and have consequence on the value of the results. The Comprehension Normalization Method is a new method of investigation that will continue to be used as a mode of inquiry across many different progressions of today's categorizations, but always done hopefully using our best knowledge of the division at the time. As our understanding of the diseases and hence our prior information change, the results of the Comprehension Normalization Method change to. It is just a method of inquiry no matter the imperfect and always incomplete state of the data.

Class of Problems II

It has been asked whether the two data sets had to share a common vocabulary. I describe two answers that didn't require that to be 100% true, that being, that the tool can work on a graduated scale to get two data sets to become in the same vocabulary, and the second being that the resonance function could be set to find less strictly defined resonance. Generally speaking though, the two sides, while they are different languages/networks, will usually have similar vocabulary or similar nodes.

We will find this class of problems in networks. In a network there are nodes and edges; in category language, nodes would be equivalent to members of a category. A category could be complex and defined more broadly to include a cluster or module of nodes (like disease module/disease causal networks could each be a category, those categories being diseases and because it is more complex, members of the module may even share emergent properties class-wide instead of just simple qualities) or alternatively the category/cluster can be defined concretely i.e. concretely tied to the type of network by only including direct adjacencies under different edge constructions these would usually be smaller clusters, and the shared qualities would be tied more specifically to the nodes'/members' relationship to the edge construction, instead of complex relationships made out of using modules or causal networks. With larger clusters (categories with a lot of members) you would begin doing the measures of resonance on populations, using proportions instead of absolute number requirements to find representative members of the class. I've read that larger modules are generally less factorizable than smaller modules. I would expect that might also mean broader modules would be more heterogeneous with respect to qualities qualifying them for a category and potentially to a degree that it could make it harder for larger modules to category-wide represent many uniform qualities at all (except high level qualities as a consequence of the category). I would also expect that there are different techniques that could get good information from the broad modules. One such for example, is to use very specific parameters to choose the nodes to use, like a very narrowly defined data set, because then it will have more homogeneous forces (on qualities)

affecting the whole data set, and would allow more fruitful results even with large/broad modules. Alternatively, when you have a lot of very small categories (direct neighbor type of categories) but a lot of them, the results, the new meta-clusters, are easier to find, and more specific. Both could produce interesting results from the Comprehension Normalization Method. I am not yet sure what the best cluster/module size is for performing the Comprehension Normalization Method. I think we would have to test the biological validity of the results to find out. But I believe the best type of network data to begin with would be ones with hundreds of modules/clusters because if the data is only broken up into two clusters, it would not be able to do the back and forth more than once and would not produce any interesting results. The worked out example later is done with many (hundreds) of small (2-5 member) categories/clusters. The worked out example proves that small but overlapping clusters do not work, but the final example will show that large highly differentiated between clusters, clusters works the best.

I'm going to describe some different networks that could make interesting comparisons. These examples all come from biology, but the examples could easily come from other fields as well.

One example data to use could be, to see a Gene Disease Network (GDN) (where diseases are the nodes and they are linked if they share a gene) by a Protein-Protein Disease Network (PPDN) (where diseases are the nodes and they are linked if they share interacting proteins). So the categorization is where the categories are the protein-interactions and the members are the diseases, and the categorization on the other side is where the categories are genes and the members are the diseases. Qualities that the two categorizations could have would be qualities of the relationship between protein interaction with disease, and qualities of the relationship between genes with disease. Instead of the one side being a Gene Disease Network, it could alternatively be a Metabolite Disease Network, where the diseases are nodes, linked if they share adjacent metabolic reactions. Making the categories be the metabolic reactions and the members be the diseases. Or alternatively further, any of the three previously mentioned disease networks from this paragraph, being compared with an miRNA Disease Network where again, the nodes are diseases, linked if they have associated genes that are targeted by at least one common miRNA molecule.

The next example data to use could be to study one Tissue-to-Tissue Coexpression (TTC) Network by another like: your Liver-Hypothalamus TTC network by, your Adipose-Hypothalamus TTC Network, where you have the choice to use the larger clusters from the bipartite graph as categories, or to take from the bipartite graph of co-expression between liver genes and hypothalamus genes, the hypothalamus genes as categories, and all liver genes co-expressed with that hypothalamus gene as the members of the category. And in the second graph, the hypothalamus genes as categories, and the adipose genes coexpressed with that hypothalamus gene as the members of that category. Qualities that the two categorizations could have would be qualities of the relationship between the hypothalamus and liver gene expression and the hypothalamus and adipose gene expression, where grouping one version of hypothalamus cell signaling to the adipose tissue by hypothalamus cell signaling to the liver could isolate a unique subset of cell signaling with something preserved between cell signaling to the adipose tissue and the liver.

The next example data to use could be, to see a tissue specific Gene Coexpression Network (GCN) (where genes are the nodes and they are linked if they are coexpressed) by a Gene Coexpression Network (GCN) for a second tissue (where again genes are the nodes and they are linked if they share coexpression). Here again you would have a choice whether to use the bigger module sized clusters as categories, or to make smaller categories with only all adjacent genes coexpressed together as the members to the category. Choosing to study larger clusters could make the shared element more high order. Joint qualities that the two categorizations could have, could be the ability to see one tissue from the perspective of another if both are regulated by a $3^{rd}$ like the brain.

Another example, which may or may not be interesting, would be to view one tissue's Protein-Protein Interaction Network, by a Protein-Protein Interaction Network of a second tissue. The categories would be the physical interactions, and the members would be the proteins. Alternatively a Comprehension Normalization Method comparison could be done instead between two Protein-Protein Interaction Networks, both in the same tissue, but one from people with the disease phenotype and the other without. Qualities that the two categorizations could have overlap found in, would be qualities of the relationship between the physical interactions with proteins when healthy, and qualities of the relationship between the physical interaction with proteins when diseased.

Another example of comparing one network by another, would be to use the Comprehension Normalization Method to compare one 'Patients Like Me' Network, where the patients are connected by certain dimensions, with a 'Patients Like Me' Network where the patients are connected by other dimensions. The categories would be the categories of the dimension the patients are connected under. And the nodes/members of the categories would be the patients. And qualities that the two categorizations could have would be qualities of the relationship between that dimension with patients, and qualities of the relationship between the other dimension with patients.

Another example, would be to view a "Drug Patient Network" by a "Side Effect Patient Network" where with a bipartite graph of patients with drugs and another one of patients with side effects, the categories would be the drugs and the patients connected to that drug are the members of that category, and on the other side, the categories are side effects and the patients connected to that side effect are the members of that side effect category. Qualities that the two categorizations could have overlap in would be qualities of the relationship between the drug with patients, and qualities of the relationship between the side effects with patients. I will show later why this comparison may have non-ideal components.

A last, other example, would be to view a Gene Coexpression Network (where the nodes are genes connected if they are coexpressed), by a Gene Protein Network, (where the nodes are genes connected if they share an interacting protein).

In the last presentation you saw diseases as categories whose members were genes and body parts as categories whose members were genes. You can think of that as viewing the Disease Gene Network by the Body Part Gene Network with the two networks as the two languages.

Comparison to Other Methods III

The following would be an alternate way to perform the Comprehension Normalization Method to achieve similar results. So using the resulting clusters generated from two separate bipartite graphs, as two sides of a third bipartite graph and then perform bipartite hierarchical clustering with the two graphs' resulting clusters as nodes and generate two dendrograms—where it looks for the closest cluster-node but across the graph and two cluster-nodes become connected in one of the trees when they become connected to the same cluster/meta-cluster on the other side. The branches of those two dendrograms, under true co-governance would be similar to those formed by the Comprehension Normalization Method performed normally, when the bipartite clustering is set up using the previous graphs as starting clusters, if things went perfectly. Using Comprehension Normalization used normally to make the clusters would be easier, and would both usually produce better results and provide additional information to help you evaluate the quality of the concluding hypotheses as will be described in the next section. So it would be preferential if you wanted those results.

Software Details, Technical Details, Worked Example IV

I'm going to go into one of the examples above to illustrate resonance algorithms with populations and then I will go into a worked out example, but one that uses smaller but numerous clusters. The two examples represent two (of many) different cluster-types from a computational standpoint. In the first example, the clusters are large enough that resonance would be measured on populations and have different calculating properties than very sparse clusters. In the second example the clusters are very small so the Comprehension Normalization Method has less complexity. You like to think higher dimensionally-so I think eventually you will use the Comprehension Normalization Method with very complex forms of clusters with directions and layers of interactions. In the first example the clusters are large, but their membership is still simple.

The first example is, as stated in the previous section, the "Drug Patient Network" by a "Side Effect Patient Network" where with a bipartite graph of patients with drugs and another one of patients with side effects, the categories would be the drugs and the patients connected to that drug are the members of that category, and on the other side, the categories are side effects and the patients connected to that side effect are the members of that side effect category. I am first going to explain it and then I will explain the parts that are not ideal for the comparison.

In the example with the drugs and side effects because we are calculating with populations, membership representing a quality key to a category must then be significantly represented lest, in the numerous members, it only represent an aberrant quality not essential to the category membership. If the side effect mini-category has a solid percentage of the drug category members (like 25%. i.e. has enough members in it that the members are probably typical of the class on this quality) then the category determinative quality is not aberrant to the side effect category, but rather with the members with the quality being a representative portion of the side effect category, the quality is extended to the rest of the side effect class. Beginning with the population in a single drug category, maybe two side effects have a significant percentage of that drug's members in them. The populations of the two side effects are combined into a meta-starting cluster that then looks for its population within all of the drug clusters. Again, with substantial membership of those side effects within a drug's population, the decisive quality can be considered class-wide in the drugs chosen as resonant. If as the starting meta-drug population increases, it specifically seems to target a side effect whose popularity at first classed out the first drug members from reaching a substantial percentage, then as the sending drug becomes a meta-drug category, and that side effect reaches representative quality of members of the meta-category, it will eventually be picked up. This back and forth expanding class-wide will find the instances of the determinative quality in both sets.

So in the example, one drug (the starting cluster) picks up two side effects whose side effect populations are significantly represented by members from that drug. (Maybe 25% of that side effect's population resonates with that drug's population.) We assume both side effects have the property of this drug/side effect categorization shared quality and the side effects become a meta-cluster and are sent back to the drug categorizations to look for members of the side effects' meta category. In the back and forth, good evidence of natural co-governance is when the next additional drugs actually fill more population for the originally chosen side effect populations; it is always good when a new addition adds population member resonance with a category already chosen. You should be able to increase the standard for resonance as you go, because if there is co-governance, then the increased size of the starting meta-category should also coincide with a larger amount of resonance with the previously chosen receiving clusters. So if you can increase the resonance standard and not lose very many previously chosen receiving clusters, then it is more likely that the act of expanding a quality to the rest of the class was natural in both instances/class types, and it is more likely that the result is a meaningful hypothesis. An additional measure to see whether it is likely that the hypothesis is meaningful is that, while generally the receiving clusters are viewed and evaluated for resonance independent of each other, for this measure, check if all of the chosen receiving clusters from that round combined are enriched for members of the meta-sending cluster and that number in co-governance, should be larger as the rounds progress further (and at least not drop). If it decreases continuously as the rounds progress and as the meta-sending cluster gets larger, then that starting cluster likely does not have any shared cluster-wide qualities with the other form of categorization (based on the categories in the categorization of today) and the hypothesis is not as meaningful. In this way increasing the resonance standard, or checking total receptive enrichment helps to reinforce the hypothesis. As a side note: adjusting the resonance standard monotonically also cures looping.

In reality, comparing a Drug Patient Network by a Side Effect Patient Network, has some problems, because the things governing a drug's relationship with patients include many molecular interactions that the patients on the same drug share with each other, whereas in things governing a side effect's relationship with patients, the patients with the same side effect only share very high order things, but on a molecular level could be very heterogeneous. This would limit the results of this Drug Patient Network comparison to only high order, though a Drug Patient Network could have very interesting small scale forces governing that could be found under a different Comprehension Normalization Method comparison.

Different comparisons, comparing the Drug Patient Network with something like an Income Patient Network (where the categories would be incomes and the members would be patients) (also high order) or some other Patient Network, would highlight different shared qualities and group the drug categories with each other around the other qualities.

Our second example is worked out. We used two data sets by the same author to achieve better vocabulary consistency across data sets. These two data sets came from one, a network of diseases united by a common implicated gene in Barabasi's paper titled "The Human Disease Network" (from 2007) and two, a network of diseases (really just disease pairs) united if they shared adjacent metabolic reactions according to the Kyoto Encyclopedia of Genes and Genomes (KEGG) Ligand database and a database of biochemically, genetically and genomically structured genome-scale metabolic network reconstructions (BiGG) from the paper titled "The Implications of Human Metabolic Network Topology for Disease Co-morbidity" (from 2008). From the visual graph of the network, we took diseases adjacent to the same gene and put those diseases into micro-clusters. Each gene was a category or cluster whose members were diseases, representative of the gene (and the gene's relationship to diseases). There were about 500 mini-categories total. Obviously often the same disease was in more than one gene category. If there was an identical cluster but connected by two different genes the identical cluster was written once for each gene. I did that because one version of the algorithm uses the frequency a disease is cited from the sending meta-cluster to help determine resonance. In later rounds of the Comprehension Normalization Method the test for resonance becomes a higher standard, measured by requiring for resonance that a receiving cluster have a greater number of members in common with the now larger meta cluster being sent or, alternatively, when fewer members resonate, they at least resonate with members very representative of the sending meta-cluster because they were mentioned many times in the sending meta-cluster. In these data, a common cause for greater representation of a disease within the sending meta-cluster is simply how well researched a disease is. Because of the bias caused by some diseases disproportionately being studied to other diseases, with this data I did not choose to include valuing the degree of representation of a disease in the sending meta-cluster as information relevant to resonance, but in other data including that information in the algorithm would be meaningful. In other data, it might be useful to use a resonance functions comprised of different clustering methods as the resonance standard. We did not use a method based standard for our resonance we used simply here the actual quantity of diseases in the receiving set matching the sending set.

Using those two data sets counted that way, the assumptions we made for this run through, were, any time two keywords from the title of a disease (from one data set's cluster) showed up in the title of a disease in the other set's cluster, that would for this trial count as referencing the same disease (discounting words like in, of, due, to, and, with, on, I, II, 1, 2, by, cancer, type, defect, disease, syndrome, deficiency, congenital, anomaly, carcinoma, linked etc.). Questionable matches, matches of only one word were not counted as resonant, unless a second disease in the cluster also matched and then both were considered resonant. It was important for the exclusion list to be comprehensive because we needed that there would be no cases of generic single words left to generate a one-word match as a second disease that is not specific. For the first few back-and-forths, any time a receiving cluster referenced any sending cluster diseases, the receiving cluster was counted as resonant. These are small clusters so even a representation of only one disease could be half or a third of the members in the class. All of the resonant receiving clusters were combined to be the sending meta-cluster in the next round. After the first two rounds, if the sending meta-cluster included more than 40 unique diseases, in order to match the increasing ease there was for a receiving cluster to be resonant, we increased the requirement to be that the receiving cluster must reference two of the sending cluster's unique diseases, (unless all of the diseases in the cluster were completely resonant, as in a one-disease cluster).

In the cases of finding true co-governance, almost all of the previously chosen receiving clusters from other rounds actually have a greater and greater percentage of their cluster become resonant so the resonant standard can increase without losing any clusters. Which is a very good sign as it means, the growing class on the other side is reconfirming that the growth, extension of membership to the rest of the class, seems accurate because the newly expanded-to members were members on the other side too. Again, in co-governance many previously identified receiving clusters' membership rose to meet that increased standard for resonance. Upon saturation for each starting metabolic disease pair cluster, the hypothesis now is that in some of the new metabolic pathway meta-groupings, the metabolic pathway mini-categories drawn together by performing the Comprehension Normalization Method with Disease Genes, share a common quality. If certain final groupings of clusters/metabolic pathways were repeated by many different starting clusters, and the clusters were preserved across increasing demands for resonance, then the researcher has a solid hypothesis that there is something this group of metabolic pathways have holding it together, and separating it from the other metabolic pathways, and can begin doing further research from there.

Character of the Results V—the Increasing Resonance Function Problems on this Data Set.

The resulting metaclusters were non-overlapping.

Because these were very small clusters (disease pairs) increasing the resonance function from one disease to two was the difference between 50% to 100% of diseases resonant for there to be a match. That is both too harsh, in a data set where the incomplete number of diseases on each side causes artificial reasons for not making a match and going 50 to 100 on an imperfect data set is going to have too high a proportion of artificial eliminations. And secondly, because we were starting at a resonance standard of one disease, for this running then every disease in the original cluster (in that initial running first round out) would have made a match unless it did not exist in the other set. Therefore, because starting at one disease resonance standard means every cluster that could not increase with the increased standard necessarily had a disease in it that is not represented on the other side, then the increase in the resonance standard test cannot work on these clusters. It is unfortunate because increasing the resonance function is a nice test of validity, but this data set simply can't. The test of increasing the resonance function can only really work when there is a cluster membership population large enough that you would not start at one, counting every instance as a match, but something greater and preferably, much greater populations in the clusters to really explore all the features.

Character of the Results V!—Domino Effect

In our running of the Comprehension Normalization Method, there were 13 metaclusters. But while studying the results from the gene disease network/metabolite disease network example we discovered something about what kind of data will and won't work for the method. In our example, the starting clusters were 2-5 disease starting clusters and because of that the resonance function had to start at 1 disease to make a match. But because these were taken off of a graph that was almost all connected, most diseases were connected to more than one gene, and so there were almost always at least one disease overlapping between every gene-based initial starting cluster (the metabolic disease clusters were similar). With a resonance function set at 1, every instance is always picked up and with the overlaps between clusters, this generates a domino effect in the formation of the final metaclusters. These final metaclusters were broken (they were not just one large metacluster), but the breaks are not for fundamental reasons, because with a resonance function smaller than the average similarity between starting clusters, it is not selective enough to be grouping by underlying forces. Rather they may be broken by things like the diseases not being in the other data set as well as genuinely being in an isolated place, just not often enough to be able to reveal genuine underlying forces. So good data to use would be larger, differentiated clusters so we can have a resonance function that can be a number larger than the amount of commonality between those clusters. This also means miniature clusters necessitating a resonance function of one, like with our example and with its overlaps, is a data set type that cannot work. We then looked into new data to run it on, with larger more differentiated clusters. Coexpression networks have larger and more differentiated clusters.

Tissue-to-Tissue Coexpression Networks VII—Worked Out Data Sample II

We tried and succeeded with a different type of data with no overlap between clusters so we could have a resonance function larger than the overlap between clusters. We choose Tissue-to-tissue Coexpression networks from the paper "Multi-tissue Coexpression Networks Reveal Unexpected Subnetworks Associated With Disease". The paper had clusters of genes that were coexpressed across tissues. The coexpression networks, had between 26 and 45 clusters of very varying sizes; there were no gene overlaps of the clusters. They used bipartite graphs for adipose and hypothalamus, liver and hypothalamus, and adipose and liver. The results from one comparison were a set of adipose genes coexpressed with hypothalamus, as well as the set of hypothalamus genes coexpressed. The same was true for the other comparisons as well. This left 6 data sets, two from each bipartite comparison and it also resulted in two data sets from two different comparisons for each of the three tissues. The two data sets of the same tissue, were for example adipose gene clusters of adipose-hypothalamus coexpression and adipose-liver coexpression. The Comprehension Normalization Method uses two different network edge constructions clustering the same set of nodes. So comparing Adipose nodes, from the Adipose-Hypothalamus comparison, and Adipose nodes from the Adipose-Liver comparison, the Comprehension Normalization Method has the two sides of the comparison, and is performed, starting with the Adipose-Hypothalamus network and then the second time starting with the Adipose-liver network. This time the gene names were the same in both sets, so a match was only made if there was a single "word" exact match between the sending metacluster's gene and the receiving cluster's gene. Because the starting clusters were of such varied size, we had to use a percentage based resonance function. The resonance function this time would measure the percentage of the receiving cluster that overlapped with any of the sending metacluster. Before running the data we were not sure which percentage for the resonance function would be appropriate on this data, but because the gene clusters between the two networks are quite different generally from each other, we only used a very small resonance function, found experimentally to be between 3-5% of the receiving cluster had to have exactly matching genes. Starting with the Adipose-Hypothalamus cluster network, the 45 clusters were grouped into a few clusters:

2, 3, 5, 7, 10, 23, 30
16, 29, 37
18, 24, 31
1, 14
11, 15
13, 39

The theory is that there is some underlying force holding these metaclusters together, and the different clusters have different qualities of that force. In this case, the large metacluster with 2, 3, 5, 7, 10, 23, and 30 happens to be the set of adipose, adipose-hypothalamus clusters that the paper we took this data from, had grouped into something called Type 2 clusters, special because they only contain genes that are trans-eQTLs but not cis-eQTLs, because the cis-eQTLs were thought to be misleading as communication drivers because instead of really driving together, they are merely expressed together because of close location. This method grouped that set of special clusters into the big metacluster, isolating it through the Comprehension Normalization Method and not through studying the eQTLs and through the Comprehension Normalization Method it grouped the ones that are the same in this way and also are the same in that they are the 7 clusters that are the most correlated with changes in the 32 mouse cross data obesity traits studied. The only cluster missing from the set of 7 this method grouped, was cluster 1, which while identified by the paper as belonging to the non cis-eQTL group, is not well correlated to changes in the 32 mouse obesity traits. We also produced results, for both, starting with the other adipose-liver network, as well as performing both of the comparison sets for liver and hypothalamus as well. In all producing 6 sets of results that we published the 3% and the 5% resonance function usage (5% is more strict and ended up with total metaclusters that were just a little bit smaller than those gathered under a resonance function of 3%). The 5 other comparisons have not been tested, against the paper's data yet, but it will be interesting to see if they too grouped the clusters that were most impactful on obesity traits together. It would also be interesting to know, what if anything is meant by the collection of the other clusters into the smaller groups. The theory of this method is that there is an underlying force, common between the two networks, that is clustering these metaclusters and these metaclusters vary because they have different values of this force. It has not been proven that there is any value to the other clusters as truly being grouped by the same force by a different value/type. It is possible only the largest cluster is meaningful within this data, but it is also possible, by this theory, that there is something in common holding the Type 2 most impactful gene coexpession clusters together, and holding the other coexpression clusters together.

In summary, the theory is the process uses the underlying (and usually unknown) reasons, uses them by proxy and strips the underlying rules holding one network architecture together and applies it to the other network. If there are commonalities in the reasons underlying each of the two networks, the end result will be meta-clusters broken by that commonality. In the resulting metaclusters, one of the underlying reasons is now exposed because it is what the bigger metaclusters have in common metacluster-wide, which would theoretically typically be different values of for each metacluster. Theoretically each comparison with a new network will break the original network up into different final resulting metaclusters with a different quality in common in the larger metaclusters, and often of a different type/value between clusters. The comparison is looking for reasons why nodes are connected the way they are (in this example, why the some genes are coexpressed across tissues) within a certain edge construction (different tissue comparisons). The quality in common with the metacluster is now one of many reasons for why the clusters are originally grouped (coexpressed). The quality/force is a reason, something that has to do with the relationship between the edge construction and the node. It is a new method of investigation to help us group subnetworks by the forces and qualities in common with another network, to understand different attributes of our subnetworks, and to divide it and understand it by more attributes with different Comprehension Normalization Method comparison. A new method of investigation.

System Illustrations and Variations

In one example implementation, any components used for processing and storing information usable in achieving the comprehension normalization procedure procedures, as discussed herein, may include non-transitory computer-readable media for storing the information. Additionally, any of components described herein, such as processing devices or user devices may include instances of a processor that can execute software or an algorithm to perform the comprehension normalization procedures, as disclosed in this Specification. These devices may further keep information (e.g., variables) in any suitable computer-readable non-transitory storage part or memory element [random access memory (RAM), ROM, EPROM, EEPROM, ASIC, etc.], software, hardware, or in any other suitable component, device, element, or object where appropriate and based on particular needs. Any of the memory items discussed herein (e.g., database, tables, trees, cache, etc.) should be construed as being encompassed within the broad term 'memory element.' Similarly, any of the potential processing elements, modules, and machines described in this Specification should be construed as being encompassed within the broad term 'processor.' Each of the components described herein can also include suitable interfaces for receiving, transmitting, and/or otherwise communicating data or information in a network environment.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The particular embodiments of the present disclosure may readily include a system on chip (SOC) central processing unit (CPU) package. An SOC represents an integrated circuit (IC) that integrates components of a computer or other electronic system into a single chip. It may contain digital, analog, mixed-signal, and radio frequency functions: all of which may be provided on a single chip substrate. Other embodiments may include a multi-chip-module (MCM), with a plurality of chips located within a single electronic package and configured to interact closely with each other through the electronic package. In various other embodiments, the digital signal processing functionalities may be implemented in one or more silicon cores in Application Specific Integrated Circuits (ASICs), Field Programmable Gate Arrays (FPGAs), and other semiconductor chips.

In example implementations, at least some portions of the processing activities outlined herein may also be implemented in software. In some embodiments, one or more of these features may be implemented in hardware provided external to the elements of the disclosed figures, or consolidated in any appropriate manner to achieve the intended functionality. The various components may include software (or reciprocating software) that can coordinate in order to achieve the operations as outlined herein. In still other embodiments, these elements may include any suitable algorithms, hardware, software, components, modules, interfaces, or objects that facilitate the operations thereof.

In one example embodiment, any number of embodiments disclosed herein may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements (e.g., storage or memory elements), etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself.

Any suitably-configured processor component can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof. In operation, processors may store information in any suitable type of non-transitory storage medium (for example, random access memory (RAM), read only memory (ROM), field programmable gate array (FPGA), erasable programmable read only memory (EPROM), electrically erasable programmable ROM (EEPROM), etc.), software, hardware, or in any other suitable component, device, element, or object where appropriate and based on particular needs. Further, the information being tracked, sent, received, or stored in a processor could be provided in any database, register, table, cache, queue, control list, or storage structure, based on particular needs and implementations, all of which could be referenced in any suitable timeframe. Any of the memory items discussed herein should be construed as being encompassed within the broad term 'memory' or 'memory element'. Similarly, any of the potential processing elements, modules, and machines described herein should be construed as being encompassed within the broad term 'microprocessor' or 'processor.'

Computer program logic implementing all or part of the functionality described herein is embodied in various forms, including, but in no way limited to, a source code form, a computer executable form, and various intermediate forms (for example, forms generated by an assembler, compiler, linker, or locator). In an example, source code includes a series of computer program instructions implemented in various programming languages, such as an object code, an assembly language, or a high-level language such as OpenCL, Fortran, C, C++, JAVA, or HTML for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims. The 'means for' in these instances (above) can include (but is not limited to) using any suitable component discussed herein, along with any suitable software, circuitry, hub, computer code, logic, algorithms, hardware, controller, interface, link, bus, communication pathway, etc. In a second example, the system includes memory that further comprises machine-readable instructions that when executed cause the system to perform any of the activities discussed above.

Note that all optional features of the apparatus described above may also be implemented with respect to the method or process described herein and specifics in the examples may be used anywhere in one or more embodiments.

In accordance with the well-established principle that an "applicant is entitled to be his or her own lexicographer," MPEP 2111.01(IV), citing In re *Paulson,* 30 F.3d 1475, 1480 (Fed. Cir. 1994), certain terms have been expressly defined herein. It is expressly intended that those terms have the definitions supplied, and that they not be given any interpretation inconsistent with those definitions.

Examples from the Previous Comprehension Normalization Method

From the previous comprehension normalization method language is a method for normalizing comprehension of a first data set and a second data set, the first data set comprising a first set of parts, and the second data set comprising a second set of parts, the method comprising: identifying one or more first-resonating parts in the second set of parts having resonance with a first part of the first set of parts using a resonance function; combining the one or more first-resonating parts in the second set into a first intermediate data set; and identifying one or more second-resonating parts in the first set of parts having resonance with the first intermediate data set using the resonance function.

What is claimed is:

1. A method for finding underlying categorization factors and forming metaclusters based on the underlying categorization factors, comprising:
    connecting nodes into a first set of clusters under a first edge construction;
    connecting the same nodes into a second set of clusters under a second edge construction, wherein the second edge construction is different from the first edge construction;
    identifying one or more first matching clusters in the second set of clusters based on a function, wherein each first matching cluster has sufficient proportion or amount of members that are similar to members of a starting cluster of the first set of clusters, and a threshold proportion or amount used in the function for identifying matching clusters depends on one or more characteristics of an overlap in membership of two clusters;
    forming a first metacluster comprising the one or more first matching clusters;
    identifying one or more second matching clusters in the first set of clusters based on the function, wherein each second matching cluster has sufficient proportion or amount of members that are similar to members of the first metacluster;
    forming a second metacluster comprising the one or more second matching clusters; and
    iteratively repeating the forming and identifying steps until a final metacluster being formed is the same with respect to a metacluster formed by a previous iteration of the forming and identifying steps.

2. The method of claim 1, wherein the first metacluster exposes a first quality or value of a first underlying categorization force, and the second metacluster exposes a second quality or value of the first underlying categorization force.

3. The method of claim 1, wherein the first metacluster exposes a first quality or value of a first underlying categorization force, and the second metacluster exposes a second quality or value of a second underlying categorization force different from the first underlying categorization force.

4. The method of claim 1, wherein the sufficient proportion or amount is associated with a function that changes with respect to one or more of the following: a number of iterations of the identifying and forming steps, and a characteristic(s) of a metacluster.

5. The method of claim 1, wherein the first set of clusters is different from the second set of clusters.

6. The method of claim 1, wherein:
the sufficient proportion or amount of membership in a first matching cluster is weighted; and
the sufficient proportion or amount of membership in a second matching cluster is weighted.

7. The method of claim 1, wherein:
connecting the nodes into the first set of clusters comprises performing one or more of the following: biclustering, multiview clustering, and hierarchical clustering; and/or
connecting the nodes into the second set of clusters comprises performing one or more of the following: biclustering, multiview clustering, and hierarchical clustering.

8. The method of claim 1, wherein:
the nodes comprise biological network data.

9. The method of claim 1, wherein:
the nodes comprise one or more of the following: nodes in defense networks, nodes in advertising networks, and nodes in finance networks.

10. The method of claim 1, further comprising:
varying the threshold proportion or the amount based on quantity of members in the overlap in membership between the two clusters.

11. The method of claim 1, wherein:
the nodes in the first set of clusters are further connected under a third edge construction; and/or
the nodes in the second set of clusters are further connected under a fourth edge construction.

12. A system for finding underlying categorization factors and forming metaclusters based on the underlying categorization factors, the system comprising,
one or more processors,
one or more memory elements to store a first set of clusters having nodes connected under a first edge construction and a second set of clusters having similar nodes connected under a second edge construction different from the first edge construction, and
a metacluster forming module, that when executed by the one or more processors is configured to:
based on a function and a starting cluster in the first set of clusters, determine one or more first matching clusters in the second set of clusters, wherein each first matching cluster has sufficient quantity of members in common with respect to the starting cluster, and a threshold quantity used in the function for determining matching clusters depends on one or more characteristics of an overlap in membership of two clusters;
based on the function and the one or more first matching clusters grouped as a first metacluster, determine one or more second matching clusters in the first set of clusters, wherein each second matching cluster has sufficient quantity of members in common with respect to the first metacluster; and
iteratively repeat the determining steps to group further metaclusters for a number of iterations to expose one or more underlying categorization factors.

13. At least one machine readable non-transitory storage medium having instructions stored thereon, wherein the instructions when executed by one or more processors cause the one or more processors to perform operations for forming metaclusters based on a first set of clusters connecting nodes under a first context and a second set of clusters connected same or similar nodes under a second, different context, the operations comprising:
identifying one or more first resonating clusters in the second set of clusters based on a function, each first resonating cluster having sufficient overlap in membership with a first cluster of the first set of clusters according to a resonance function, wherein an overlap threshold used in the function for identifying resonating clusters depends on one or more characteristics of an overlap in membership of two clusters;
combining the one or more first resonating clusters in the second set of clusters into a first metacluster;
identifying one or more second resonating clusters in the first set of clusters based on the function, each second resonating cluster having sufficient overlap in membership with the first metacluster according to the resonance function;
combining the one or more second resonating clusters in the first set of clusters into a second metacluster; and
repeating the identifying and combining steps until metaclusters exposing underlying categorization forces reach saturation.

14. The system of claim 12, wherein:
determining the one or more first matching clusters comprises determining that a first quantity of members of a first matching cluster is sufficiently representative of the starting cluster equal to or exceeds a first threshold; and
determining the one or more second matching clusters comprises determining that a second quantity of members of a second matching cluster is sufficiently representative of the first metacluster equal to exceeds a second threshold.

15. The system of claim 12, wherein the metacluster forming module is further configured to:
change the threshold quantity used for determining sufficiency in quantity between iterations.

16. The system of claim 12, wherein the metacluster forming module is further configured to:
iteratively repeat the determining steps with a different starting cluster in the first set of cluster to expose one or more other underlying categorization factors.

17. The at least one machine readable non-transitory storage medium of claim 13, wherein identifying one or more first resonating clusters comprises:
determining, based on the resonance function, that sufficient percentage of members of a first resonating cluster is representative of the first cluster.

18. The at least one machine readable non-transitory storage medium of claim 13, wherein identifying one or more second resonating clusters comprises:
determining, based on the resonance function, that sufficient percentage of members of a second resonating cluster is representative of the first metacluster.

19. A method for finding underlying categorization factors and forming metaclusters based on the underlying categorization factors, comprising:

using a first set of clusters having nodes connected under a first edge construction;

using a second set of clusters having the same nodes connected under a second edge construction, wherein the second edge construction is different from the first edge construction;

identifying one or more first matching clusters in the second set of clusters based on a function, wherein each first matching cluster a sufficient portion of members common with a starting cluster of the first set of clusters, and a threshold proportion or amount used in the function for identifying matching clusters depends on one or more characteristics of an overlap in membership of two clusters;

forming a first metacluster comprising the one or more first matching clusters;

identifying one or more second matching clusters in the first set of clusters based on the function, wherein each second matching cluster a sufficient portion of members in common with the first metacluster;

forming a second metacluster comprising the one or more second matching clusters; and iteratively repeating the forming and identifying steps until a final metacluster being formed is the same with respect to a metacluster formed by a previous iteration of the forming and identifying steps.

20. The method of claim 19, wherein the function changes with respect to one or more of the following: a number of iterations of the identifying and forming steps, and characteristic(s) of a metacluster.

* * * * *